US007541515B2

(12) United States Patent
Hood et al.

(10) Patent No.: US 7,541,515 B2
(45) Date of Patent: Jun. 2, 2009

(54) METHOD OF INCREASING EXPRESSION OF HETEROLOGOUS PROTEINS IN PLANTS

(75) Inventors: Elizabeth Hood, College Station, TX (US); John Howard, College Station, TX (US); Donna Delaney, College Station, TX (US)

(73) Assignee: ProdiGene, Inc., Adel, IA (US)

( * ) Notice: Subject to any disclaimer, the term of this patent is extended or adjusted under 35 U.S.C. 154(b) by 775 days.

(21) Appl. No.: 10/252,732

(22) Filed: Sep. 23, 2002

(65) Prior Publication Data

US 2003/0145346 A1 Jul. 31, 2003

Related U.S. Application Data

(60) Provisional application No. 60/324,308, filed on Sep. 24, 2001.

(51) Int. Cl.
*C12N 15/82* (2006.01)
(52) U.S. Cl. ........................ 800/278; 800/276
(58) Field of Classification Search ................. 800/260, 800/264, 269, 278, 281, 287; 435/468
See application file for complete search history.

(56) References Cited

U.S. PATENT DOCUMENTS

| 5,750,848 | A | 5/1998 | Kruger et al. ............... 800/281 |
| 6,091,002 | A | 7/2000 | Asrar et al. ................. 800/288 |
| 6,121,524 | A | 9/2000 | Chapman ................. 800/320.1 |
| 6,127,602 | A | 10/2000 | Nichols ....................... 800/284 |
| 6,127,603 | A | 10/2000 | Nichols ....................... 800/284 |
| 6,288,304 | B1 * | 9/2001 | Moloney et al. ............ 800/288 |
| 2002/0088020 | A1 * | 7/2002 | Leto et al. ................... 800/275 |

FOREIGN PATENT DOCUMENTS

| WO | WO9839461 | 10/1998 |
| WO | WO0149852 | 7/2001 |

OTHER PUBLICATIONS

Stevens et al. 2000. 124: 173-182.*
Goddijn et al. 1995. Trends in Biotechnology 13(9): 379-387.*
Hood et al. 1997. Molecular Breeding 3: 291-306.*
Lambert et al. 1998. Agron. J. 90: 211-215.*
Wikipedia, the free encyclopedia, retrieved from http://en.wikipedia.org/wiki/Monocotyledons on May 23, 2007, p. 1-4.*
Qiu, L. et al. Preliminary study on accumulation characteristics of protein and oil in developing soyabean seeds, Scientia Agricultura sinica, (1990) vol. 23, No. 5, pp. 28-32. 7 ref., Abstract only.
Zhou, Z. et al. Research on correlation of upland cotton seed and fibre quality with temperature in bolling period. Shaanxi Journal of Agricultural Sciences, (1992) No. 3, pp. 3-5. 4 ref., Abstract only.
Xia, R. et al. Study on the characteristics of lint quality and seed quality of low gossypol cotton. China Cottons, (1989) No. 5 pp. 23-25, Abstract only.
Gururajan, K. N. et al. Yield and seed-quality characteristics of varieties of glandless cotton (Gossypium hirsutum). Indian Journal of Agricultural Sciences vol. 62 (5): p. 316-318, 1992, Abstract only.
Kovacs-Schneider, M. et al. Breeding maize for oil and protein content of the grain. Novenytermeles vol. 35 (5): p. 383-389. 1986, Abstract only.
Craig E. Coleman, et al. Expression of a mutant β-zein creates the floury2 phenotype in transgenic maize. Proc. Natl. Acad. Sci. USA vol. 94, pp. 7094-7097, Jun. 1997.
Robert J. Lambert, et al. A High Oil Pollinator Enhancement of Kernel Oil and Effects on Grain Yields of Maize Hybrids. Published in Agron. J, 90:211-215 (1998).
D.E. Alexander. Oil Content Versus Grain Yield In Corn. Maydica 44 (1999):111-112.
M.B. Letchworth, et al. Pollen Parent Effects on Oil, Protein and Starch Concentration in Maize Kernels. Published in Crop Sci. 38:363-367 (1998).
Dinakar Bhattramakki, et al. Expression of genes encoding globuin and prolamin storage proteins in kernels of Illinois Long Term Chemical Selection Strains. Crop Sci. 36:1029-1036 (1996).
Drew Schwartz, Analysis of the Size Alleles of the Pro Gene in Maize-Evidence for a Mutant Protein Processor. Molec. Gen. Genet. 174, 233-240 (1979).
Faith C. Belanger, et al. Molecular Basis for Allelc Polymorphism of the Maize Globulin-1 Gene. Genetics 129: 863-872 (Nov. 1991).
Mauricio A. Lopes, et al. Synthesis of an unusual β-zein protein is correlated with the phenotypic effects of the floury2 mutation in maize. Mol Gen Genet (1994) 245:537-547.
Alan L. Kriz, Characterization of Embryo Globulins Enlcoded by the Maize Gib Genes. Biochemical Genetics, vol. 27, Nos. ¾, 1989.
J.L. Puckett, et al. Globulin Gene Expressio In Opaqe-2 And Floury-2 Mutant Maize Embryos. Maydic 36 (1991): 161-167.
F. Salamini, et al. Mucronate, Mc, a dominant gene of maize which interacts with opague-2 to suppress zein synthesis. Theor Appl Genet (1983) 65: 123-128.
Takiwa, Fumio, "Development of High Accumulation Systems in Rice Endosperm" Abstract, New Frontier of Plant Molecular Farming; NIAR, Tsukuba City Japan, Mar. 7-8, 2000.
Momma et al. "Quality and Safety Evaluation of Genetically Engineered Rice with Soybean Glycinin: Analyses of the Grain Composition and Digestibility of Glycinin in Transgenic Rice" Biosciences, Biotechnology and Biochemistry 1999. Vol. 63, No. 2, 314-318.
Anzai et al., "Production of human lactoferrin in transgenic plants" Lactoferrin: Structure, Funcation and Applications. Edit. K. Shimazaki et al. Amsterdam: Elxeview Science B.V., 2000, 265-271.

(Continued)

*Primary Examiner*—David H Kruse
*Assistant Examiner*—Keith O. Robinson
(74) *Attorney, Agent, or Firm*—Patricia A. Sweeney

(57) ABSTRACT

Increased expression of heterologous proteins in a plant is achieved by introducing the nucleotide sequence encoding the heterologous protein into a plant that has high oil seed content compared to low oil seed and/or is introduced into a plant having reduced alcohol soluble proteins in the endosperm. The nucleotide sequence may be introduced by direct transformation into the plant, or by direct transformation into another plant, and crossing with the high oil plant or plant have reduced levels of alcohol soluble protein in the endosperm. Further, the nucleotide sequences may be introduced into one or both of the high oil plant and the plant having reduced levels of alcohol soluble proteins, and the plants may be crossed to result in a progeny having even further increased expression levels of the heterologous protein.

6 Claims, 20 Drawing Sheets

OTHER PUBLICATIONS

Kovacs-Schneider et al., "Dynamics of accumulation of sotred material and change of water content in Opaque-2 and normal maize kernesl" Acta Agronomica Academiae Scientiarum Hungaricae, 1984, vol. 33 No. 3-4, 387-402.

Hood et al. "Commercial production of avidin from transgenic maize: characterization of transformant, production, processing, extraction and purification" Molecule Breeding: New Strategies in Plant Improvement, Kluwer Academic Pub. NL. No. 3, Aug. 1998 pp. 291-306.

* cited by examiner

Figure 2A

```
       gccatcgggccggtggcgagcctcgtcgtcgcgaacgccccgtctcgcccgacggcttc
  1    ---------+---------+---------+---------+---------+---------+   60
       cggtagcccggccaccgctcggagcagcagcgcttgcgggggcagagcgggctgccgaag
        A  I  G  P  V  A  S  L  V  V  A  N  A  P  V  S  P  D  G  F cttcgggatgccatcgtggtcaacggcgtggtcccttccccgctcatcaccgggaagaag
 61    ---------+---------+---------+---------+---------+---------+  120
       gaagccctacggtagcaccagttgccgcaccagggaaggggcgagtagtggcccttcttc
        L  R  D  A  I  V  V  N  G  V  V  P  S  P  L  I  T  G  K  K ggagaccgcttccagctcaacgtcgtcgacaccttgaccaaccacagcatgctcaagtcc
121    ---------+---------+---------+---------+---------+---------+  180
       cctctggcgaaggtcgagttgcagcagctgtggaactggttggtgtcgtacgagttcagg
        G  D  R  F  Q  L  N  V  V  D  T  L  T  N  H  S  M  L  K  S actagtatccactggcacggcttcttccaggcaggcaccaactgggcagacggacccgcg
181    ---------+---------+---------+---------+---------+---------+  240
       tgatcataggtgaccgtgccgaagaaggtccgtccgtggttgaccegtctgcctgggcgc
        T  S  I  H  W  H  G  F  F  Q  A  G  T  N  W  A  D  G  P  A ttcgtcaaccagtgccctattgcttccgggcattcatttctgtacgacttccatgtgccc
241    ---------+---------+---------+---------+---------+---------+  300
       aagcagttggtcacgggataacgaaggcccgtaagtaaagacatgctgaaggtacacggg
        F  V  N  Q  C  P  I  A  S  G  H  S  F  L  Y  D  F  H  V  P gaccaggcaggaacgttctggtaccacagtcatctgtctacgcaatactgtgacgggctg
301    ---------+---------+---------+---------+---------+---------+  360
       ctggtccgtccttgcaagaccatggtgtcagtagacagatgcgttatgacactgcccgac
        D  Q  A  G  T  F  W  Y  H  S  H  L  S  T  Q  Y  C  D  G  L cgaggaccgttcgtcgtgtacgaccccaaggatccgcacgccagccgctacgatgttgac
361    ---------+-  ------+---------+---------+---------+---------+  420
       gctcctggcaagcagcacatgctggggttcctaggcgtgcggtcggcgatgctacaactg
        R  G  P  F  V  V  Y  D  P  K  D  P  H  A  S  R  Y  D  V  D aacgagagcacggtcatcacgttgaccgactggtaccacaccgctgcccggctcggtccc
421    ---------+---------+---------+---------+---------+---------+  480
       ttgctctcgtgccagtagtgcaactggctgaccatggtgtggcgacgggccgagccaggg
        N  E  S  T  V  I  T  L  T  D  W  Y  H  T  A  A  R  L  G  P
```

Figure 2B

```
     aggttcccactcggcgcggacgccacgctcatcaatggtcttggcggtcggcctccact
481  ---------+---------+---------+---------+---------+---------+  540
     tccaagggtgagccgcgcctgcggtgcgagtagttaccagaacccgccagccggaggtga
      R  F  P  L  G  A  D  A  T  L  I  N  G  L  G  R  S  A  S  T cccaccgccgcgcttgctgtgatcaacgtccagcacggaaagcgctaccgcttccgtctc
541  ---------+---------+---------+---------+---------+---------+  600
     gggtggcggcgcgaacgacactagttgcaggtcgtgccttcgcgatggcgaaggcagag
      P  T  A  A  L  A  V  I  N  V  Q  H  G  K  R  Y  R  F  R  L gtttcgatctcgtgcgacccgaactacacgttcagcatcgacgggcacaatctgaccgtc
601  ---------+---------+---------+---------+---------+---------+  660
     caaagctagagcacgctgggcttgatgtgcaagtcgtagctgcccgtgttagactggcag
      V  S  I  S  C  D  P  N  Y  T  F  S  I  D  G  H  N  L  T  V atcgaggtcgacggtatcaacagccagcctctccttgtcgactctatccagatcttcgcc
661  ---------+---------+---------+---------+---------+---------+  720
     tagctccagctgccatagttgtcggtcggagaggaacagctgagataggtctagaagcgg
      I  E  V  D  G  I  N  S  Q  P  L  L  V  D  S  I  Q  I  F  A gcgcagcgctactcctttgtgttgaatgcgaaccaaacggtcggcaactactgggtccgc
721  ---------+---------+---------+---------+---------+---------+  780
     cgcgtcgcgatgaggaaacacaacttacgcttggtttgccagccgttgatgacccaggcg
      A  Q  R  Y  S  F  V  L  N  A  N  Q  T  V  G  N  Y  W  V  R gcgaacccgaacttcggaacggttgggttcgccggggggatcaactccgccatcctgcgc
781  ---------+---------+---------+---------+---------+---------+  840
     cgcttgggcttgaagccttgccaacccaagcggccccctagttgaggcggtaggacgcg
      A  N  P  N  F  G  T  V  G  F  A  G  G  I  N  S  A  I  L  R taccaaggcgcaccagtcgccgagcccactacgacccagacgacgtcggtgatcccgctt
841  ---------+---------+---------+---------+---------+---------+  900
     atggttccgcgtggtcagcggctcgggtgatgctgggtctgctgcagccactagggcgaa
      Y  Q  G  A  P  V  A  E  P  T  T  T  Q  T  T  S  V  I  P  L atcgagacgaacttgcaccccctcgctcgcatgcctgtgcctggcagcccgacacccggg
901  ---------+---------+---------+---------+---------+---------+  960
     tagctctgcttgaacgtggggagcgagcgtacggacacggaccgtcgggctgtgggccc
      I  E  T  N  L  H  P  L  A  R  M  P  V  P  G  S  P  T  P  G ggcgtcgacaaggcgctcaacctcgcgtttaacttcaacggcaccaacttcttcatcaac
961  ---------+---------+---------+---------+---------+---------+  1020
     ccgcagctgttccgcgagttggagcgcaaattgaagttgccgtggttgaagaagtagttg
      G  V  D  K  A  L  N  L  A  F  N  F  N  G  T  N  F  F  I  N
```

Figure 2C

```
      aacgcgactttcacgccgccgaccgtcccggtactcctccagattctgagcggtgcgcag
1021  ---------+---------+---------+---------+---------+---------+  1080
      ttgcgctgaaagtgcggcggctggcagggccatgaggaggtctaagactcgccacgcgtc
      N  A  T  F  T  P  P  T  V  P  V  L  L  Q  I  L  S  G  A  Q accgcacaagacctgctccctgcaggctctgtctacccgctcccggcccactccaccatc
1081  ---------+---------+---------+---------+---------+---------+  1140
      tggcgtgttctggacgagggacgtcccgagacagatgggcgagggccgggtgaggtggtag
      T  A  Q  D  L  L  P  A  G  S  V  Y  P  L  P  A  H  S  T  I gagatcacgctgcccgcgaccgccttggccccgggtgcaccgcaccccttccacctgcac
1141  ---------+---------+---------+---------+---------+---------+  1200
      ctctagtgcgacgggcgctggcggaaccggggcccacgtggcgtggggaaggtggacgtg
      E  I  T  L  P  A  T  A  L  A  P  G  A  P  H  P  F  H  L  H ggtcacgccttcgcggtcgttcgcagcgcggggagcaccacgtataactacaacgacccg
1201  ---------+---------+---------+---------+---------+---------+  1260
      ccagtgcggaagcgccagcaagcgtcgcgccctcgtggtgcatattgatgttgctgggc
      G  H  A  F  A  V  V  R  S  A  G  S  T  T  Y  N  Y  N  D  P atcttccgcgacgtcgtgagcacgggcacgcccgccgcgggcgacaacgtcacgatccgc
1261  ---------+---------+---------+---------+---------+---------+  1320
      tagaaggcgctgcagcactcgtgcccgtgcgggcggcgcccgctgttgcagtgctaggcg
      I  F  R  D  V  V  S  T  G  T  P  A  A  G  D  N  V  T  I  R ttccagacggacaaccccgggccgtggttcctccactgccacatcgacttccacctcgac
1321  ---------+---------+---------+---------+---------+---------+  1380
      aaggtctgcctgttggggcccggcaccaaggaggtgacggtgtagctgaaggtggagctg
      F  Q  T  D  N  P  G  P  W  F  L  H  C  H  I  D  F  H  L  D gcgggcttcgcgatcgtgttcgcagaggacgttgcggacgtgaaggcggcgaacccggtt
1381  ---------+---------+---------+---------+---------+---------+  1440
      cgcccgaagcgctagcacaagcgtctcctgcaacgcctgcacttccgccgcttgggccaa
      A  G  F  A  I  V  F  A  E  D  V  A  D  V  K  A  A  N  P  V ccgaaggcgtggtcggacctgtgcccgatctacgacgggctgagcgaggctaaccagtga
1441  ---------+---------+---------+---------+---------+---------+  1500
      ggcttccgcaccagcctggacacgggctagatgctgcccgactcgctccgattggtcact
      P  K  A  W  S  D  L  C  P  I  Y  D  G  L  S  E  A  N  Q  *
```

Figure 14A

```
        A   V   C   P   D   G   T   R   V   T   N   A   A   C   C   A   F
  1 GCAGTCTGTC CAGACGGTAC CCGCGTCACC AACGCGGCGT GCTGCGCTTT
    CGTCAGACAG GTCTGCCATG GGCGCAGTGG TTGCGCCGCA CGACGCGAAA
        I   P   L   A   Q   D   L   Q   E   T   L   F   Q   G   D   C
 51 CATTCCGCTC GCACAGGACT TGCAAGAGAC TCTGTTCCAG GGTGACTGTG
    GTAAGGCGAG CGTGTCCTGA ACGTTCTCTG AGACAAGGTC CCACTGACAC
        G   E   D   A   H   E   V   I   R   L   T   F   H   D   A   I   A
101 GCGAAGATGC CCACGAAGTC ATCCGTCTGA CCTTCCACGA CGCTATTGCA
    CGCTTCTACG GGTGCTTCAG TAGGCAGACT GGAAGGTGCT GCGATAACGT
        I   S   Q   S   L   G   P   Q   A   G   G   A   D   G   S   M
151 ATCTCCCAGA GCCTAGGTCC TCAGGCTGGC GGCGGTGCTG ACGGCTCCAT
    TAGAGGGTCT CGGATCCAGG AGTCCGACCG CCGCCACGAC TGCCGAGGTA
        L   H   F   P   T   I   E   P   N   F   S   A   N   N   G   I
201 GCTGCACTTC CCGACAATCG AGCCCAACTT CTCCGCCAAC AACGGCATCG
    CGACGTGAAG GGCTGTTAGC TCGGGTTGAA GAGGCGGTTG TTGCCGTAGC
        D   D   S   V   N   N   L   L   P   F   M   Q   K   H   D   T   I
251 ATGACTCCGT CAACAACTTG CTTCCCTTCA TGCAGAAACA CGACACCATC
    TACTGAGGCA GTTGTTGAAC GAAGGGAAGT ACGTCTTTGT GCTGTGGTAG
        S   A   A   D   L   V   Q   F   A   G   A   V   A   L   S   N   C
301 AGTGCCGCCG ATCTTGTACA GTTCGCCGGT GCGGTCGCGC TGAGCAACTG
    TCACGGCGGC TAGAACATGT CAAGCGGCCA CGCCAGCGCG ACTCGTTGAC
        P   G   A   P   R   L   E   F   M   A   G   R   P   N   T   T
351 CCCAGGTGCT CCTCGCCTCG AGTTCATGGC TGGACGTCCG AACACTACCA
    GGGTCCACGA GGAGCGGAGC TCAAGTACCG ACCTGCAGGC TTGTGATGGT
        I   P   A   V   E   G   L   I   P   E   P   Q   D   S   V   T   K
401 TCCCCGCAGT TGAGGGCCTC ATTCCTGAGC CTCAAGACAG CGTCACCAAA
    AGGGGCGTCA ACTCCCGGAG TAAGGACTCG GAGTTCTGTC GCAGTGGTTT
        I   L   Q   R   F   E   D   A   G   N   F   S   P   F   E   V   V
451 ATCCTGCAGC GCTTCGAGGA CGCCGGCAAC TTCTCGCCGT TCGAGGTCGT
    TAGGACGTCG CGAAGCTCCT GCGGCCGTTG AAGAGCGGCA AGCTCCAGCA
        S   L   L   A   S   H   T   V   A   R   A   D   K   V   D   E
501 CTCGCTCCTG GCTTCACACA CCGTTGCTCG TGCGGACAAG GTCGACGAGA
    GAGCGAGGAC CGAAGTGTGT GGCAACGAGC ACGCCTGTTC CAGCTGCTCT
        T   I   D   A   A   P   F   D   S   T   P   F   T   F   D   T   Q
551 CCATCGATGC TGCGCCCTTC GACTCGACAC CCTTCACCTT CGACACCCAG
    GGTAGCTACG ACGCGGGAAG CTGAGCTGTG GGAAGTGGAA GCTGTGGGTC
        V   F   L   E   V   L   L   K   G   T   G   F   P   G   S   N   N
601 GTGTTCCTCG AGGTCCTGCT CAAGGGCACA GGCTTCCCGG GCTCGAACAA
    CACAAGGAGC TCCAGGACGA GTTCCCGTGT CCGAAGGGCC CGAGCTTGTT
        N   T   G   E   V   M   S   P   L   P   L   G   S   G   D
651 CAACACCGGC GAGGTGATGT CGCCGCTCCC ACTCGGCAGC GGCAGCGACA
    GTTGTGGCCG CTCCACTACA GCGGCGAGGG TGAGCCGTCG CCGTCGCTGT
        T   G   E   M   R   L   Q   S   D   F   A   L   A   R   D   E   R
```

Figure 14B

```
 701  CGGGCGAGAT GCGCCTGCAG TCCGACTTTG CGCTCGCGCG CGACGAGCGC
      GCCCGCTCTA CGCGGACGTC AGGCTGAAAC GCGAGCGCGC GCTGCTCGCG
         T   A   C   F   W   Q   S   F   V   N   E   Q   E   F   M   A   A
 751  ACGGCGTGCT TCTGGCAGTC GTTCGTCAAC GAGCAGGAGT TCATGGCGGC
      TGCCGCACGA AGACCGTCAG CAAGCAGTTG CTCGTCCTCA AGTACCGCCG
         S   F   K   A   A   M   A   K   L   A   I   L   G   H   S   R
 801  GAGCTTCAAG GCCGCGATGG CGAAGCTCGC GATCCTCGGC CACAGCCGCA
      CTCGAAGTTC CGGCGCTACC GCTTCGAGCG CTAGGAGCCG GTGTCGGCGT
         S   S   L   I   D   C   S   D   V   V   P   V   P   K   P   A   V
 851  GCAGCCTCAT CGACTGCAGC GACGTCGTCC CCGTCCCGAA GCCCGCCGTC
      CGTCGGAGTA GCTGACGTCG CTGCAGCAGG GGCAGGGCTT CGGGCGGCAG
         N   K   P   A   T   F   P   A   T   K   G   P   K   D   L   D   T
 901  AACAAGCCCG CGACGTTCCC CGCGACGAAG GGCCCCAAGG ATCTCGACAC
      TTGTTCGGGC GCTGCAAGGG GCGCTGCTTC CCGGGGTTCC TAGAGCTGTG
         L   T   C   K   A   L   K   F   P   T   L   T   S   D   P   G
 951  ACTCACGTGC AAGGCCCTCA AGTTCCCGAC GCTGACCTCT GACCCCGGTG
      TGAGTGCACG TTCCGGGAGT TCAAGGGCTG CGACTGGAGA CTGGGGCCAC
         A   T   E   T   L   I   P   H   C   S   N   G   G   M   S   C   P
1001  CTACCGAGAC CCTCATCCCC CACTGCTCCA ACGGCGGCAT GTCCTGCCCT
      GATGGCTCTG GGAGTAGGGG GTGACGAGGT TGCCGCCGTA CAGGACGGGA
         G   V   Q   F   D   G   P   A
1051  GGTGTTCAGT TCGATGGCCC TGCCTGA
      CCACAAGTCA AGCTACCGGG ACGGACT
```

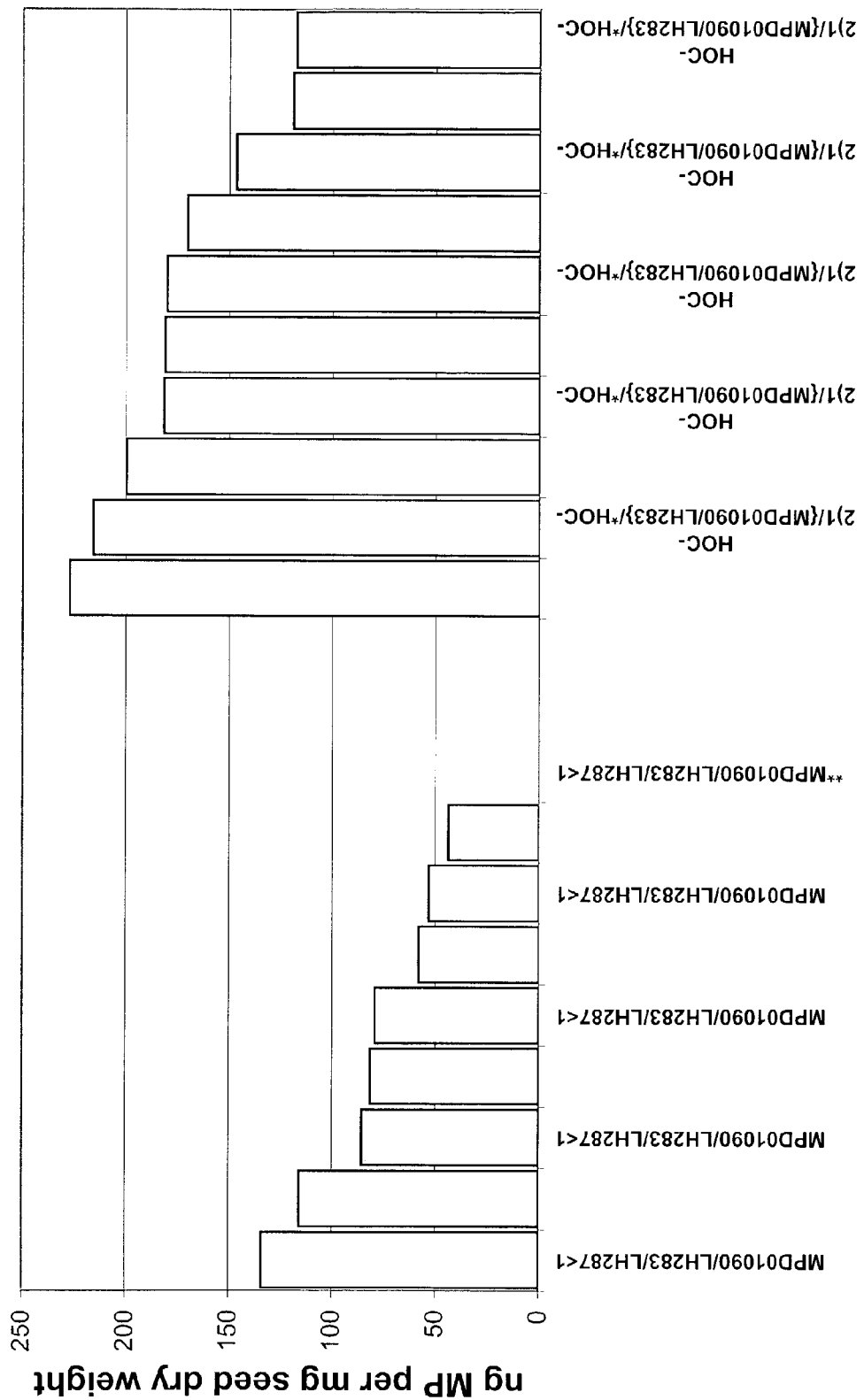

SEQUENCE LISTING

```
<160> NUMBER OF SEQ ID NOS: 8

<210> SEQ ID NO 1
<211> LENGTH: 1500
<212> TYPE: DNA
<213> ORGANISM: Unknown Organism
<220> FEATURE:
<221> NAME/KEY: CDS
<222> LOCATION: (1)..(1500)
```

<220> FEATURE:
<223> OTHER INFORMATION: Description of Unknown Organism: Laccase
    nucleotide sequence

<400> SEQUENCE: 1

| | | | | | | | | | | | | | | | | |
|---|---|---|---|---|---|---|---|---|---|---|---|---|---|---|---|---|
| gcc | atc | ggg | ccg | gtg | gcg | agc | ctc | gtc | gtc | gcg | aac | gcc | ccc | gtc | tcg | 48 |
| Ala | Ile | Gly | Pro | Val | Ala | Ser | Leu | Val | Val | Ala | Asn | Ala | Pro | Val | Ser | |
| 1 | | | | 5 | | | | | 10 | | | | | 15 | | |

| | | | | | | | | | | | | | | | | |
|---|---|---|---|---|---|---|---|---|---|---|---|---|---|---|---|---|
| ccc | gac | ggc | ttc | ctt | cgg | gat | gcc | atc | gtg | gtc | aac | ggc | gtg | gtc | cct | 96 |
| Pro | Asp | Gly | Phe | Leu | Arg | Asp | Ala | Ile | Val | Val | Asn | Gly | Val | Val | Pro | |
| | | | 20 | | | | | 25 | | | | | 30 | | | |

| | | | | | | | | | | | | | | | | |
|---|---|---|---|---|---|---|---|---|---|---|---|---|---|---|---|---|
| tcc | ccg | ctc | atc | acc | ggg | aag | aag | gga | gac | cgc | ttc | cag | ctc | aac | gtc | 144 |
| Ser | Pro | Leu | Ile | Thr | Gly | Lys | Lys | Gly | Asp | Arg | Phe | Gln | Leu | Asn | Val | |
| | | 35 | | | | | 40 | | | | | 45 | | | | |

| | | | | | | | | | | | | | | | | |
|---|---|---|---|---|---|---|---|---|---|---|---|---|---|---|---|---|
| gtc | gac | acc | ttg | acc | aac | cac | agc | atg | ctc | aag | tcc | act | agt | atc | cac | 192 |
| Val | Asp | Thr | Leu | Thr | Asn | His | Ser | Met | Leu | Lys | Ser | Thr | Ser | Ile | His | |
| 50 | | | | | 55 | | | | | 60 | | | | | | |

| | | | | | | | | | | | | | | | | |
|---|---|---|---|---|---|---|---|---|---|---|---|---|---|---|---|---|
| tgg | cac | ggc | ttc | ttc | cag | gca | ggc | acc | aac | tgg | gca | gac | gga | ccc | gcg | 240 |
| Trp | His | Gly | Phe | Phe | Gln | Ala | Gly | Thr | Asn | Trp | Ala | Asp | Gly | Pro | Ala | |
| 65 | | | | 70 | | | | | 75 | | | | | 80 | | |

| | | | | | | | | | | | | | | | | |
|---|---|---|---|---|---|---|---|---|---|---|---|---|---|---|---|---|
| ttc | gtc | aac | cag | tgc | cct | att | gct | tcc | ggg | cat | tca | ttt | ctg | tac | gac | 288 |
| Phe | Val | Asn | Gln | Cys | Pro | Ile | Ala | Ser | Gly | His | Ser | Phe | Leu | Tyr | Asp | |
| | | | 85 | | | | | 90 | | | | | 95 | | | |

| | | | | | | | | | | | | | | | | |
|---|---|---|---|---|---|---|---|---|---|---|---|---|---|---|---|---|
| ttc | cat | gtg | ccc | gac | cag | gca | gga | acg | ttc | tgg | tac | cac | agt | cat | ctg | 336 |
| Phe | His | Val | Pro | Asp | Gln | Ala | Gly | Thr | Phe | Trp | Tyr | His | Ser | His | Leu | |
| | | | 100 | | | | | 105 | | | | | 110 | | | |

| | | | | | | | | | | | | | | | | |
|---|---|---|---|---|---|---|---|---|---|---|---|---|---|---|---|---|
| tct | acg | caa | tac | tgt | gac | ggg | ctg | cga | gga | ccg | ttc | gtc | gtg | tac | gac | 384 |
| Ser | Thr | Gln | Tyr | Cys | Asp | Gly | Leu | Arg | Gly | Pro | Phe | Val | Val | Tyr | Asp | |
| | | | 115 | | | | | 120 | | | | | 125 | | | |

| | | | | | | | | | | | | | | | | |
|---|---|---|---|---|---|---|---|---|---|---|---|---|---|---|---|---|
| ccc | aag | gat | ccg | cac | gcc | agc | cgc | tac | gat | gtt | gac | aac | gag | agc | acg | 432 |
| Pro | Lys | Asp | Pro | His | Ala | Ser | Arg | Tyr | Asp | Val | Asp | Asn | Glu | Ser | Thr | |
| | | 130 | | | | | 135 | | | | | 140 | | | | |

| | | | | | | | | | | | | | | | | |
|---|---|---|---|---|---|---|---|---|---|---|---|---|---|---|---|---|
| gtc | atc | acg | ttg | acc | gac | tgg | tac | cac | acc | gct | gcc | cgg | ctc | ggt | ccc | 480 |
| Val | Ile | Thr | Leu | Thr | Asp | Trp | Tyr | His | Thr | Ala | Ala | Arg | Leu | Gly | Pro | |
| 145 | | | | | 150 | | | | | 155 | | | | | 160 | |

| | | | | | | | | | | | | | | | | |
|---|---|---|---|---|---|---|---|---|---|---|---|---|---|---|---|---|
| agg | ttc | cca | ctc | ggc | gcg | gac | gcc | acg | ctc | atc | aat | ggt | ctt | ggg | cgg | 528 |
| Arg | Phe | Pro | Leu | Gly | Ala | Asp | Ala | Thr | Leu | Ile | Asn | Gly | Leu | Gly | Arg | |
| | | | | 165 | | | | | 170 | | | | | 175 | | |

| | | | | | | | | | | | | | | | | |
|---|---|---|---|---|---|---|---|---|---|---|---|---|---|---|---|---|
| tcg | gcc | tcc | act | ccc | acc | gcc | gcg | ctt | gct | gtg | atc | aac | gtc | cag | cac | 576 |
| Ser | Ala | Ser | Thr | Pro | Thr | Ala | Ala | Leu | Ala | Val | Ile | Asn | Val | Gln | His | |
| | | | 180 | | | | | 185 | | | | | 190 | | | |

| | | | | | | | | | | | | | | | | |
|---|---|---|---|---|---|---|---|---|---|---|---|---|---|---|---|---|
| gga | aag | cgc | tac | cgc | ttc | cgt | ctc | gtt | tcg | atc | tcg | tgc | gac | ccg | aac | 624 |
| Gly | Lys | Arg | Tyr | Arg | Phe | Arg | Leu | Val | Ser | Ile | Ser | Cys | Asp | Pro | Asn | |
| | | 195 | | | | | 200 | | | | | 205 | | | | |

| | | | | | | | | | | | | | | | | |
|---|---|---|---|---|---|---|---|---|---|---|---|---|---|---|---|---|
| tac | acg | ttc | agc | atc | gac | ggg | cac | aat | ctg | acc | gtc | atc | gag | gtc | gac | 672 |
| Tyr | Thr | Phe | Ser | Ile | Asp | Gly | His | Asn | Leu | Thr | Val | Ile | Glu | Val | Asp | |
| | | 210 | | | | | 215 | | | | | 220 | | | | |

| | | | | | | | | | | | | | | | | |
|---|---|---|---|---|---|---|---|---|---|---|---|---|---|---|---|---|
| ggt | atc | aac | agc | cag | cct | ctc | ctt | gtc | gac | tct | atc | cag | atc | ttc | gcc | 720 |
| Gly | Ile | Asn | Ser | Gln | Pro | Leu | Leu | Val | Asp | Ser | Ile | Gln | Ile | Phe | Ala | |
| 225 | | | | | 230 | | | | | 235 | | | | | 240 | |

| | | | | | | | | | | | | | | | | |
|---|---|---|---|---|---|---|---|---|---|---|---|---|---|---|---|---|
| gcg | cag | cgc | tac | tcc | ttt | gtg | ttg | aat | gcg | aac | caa | acg | gtc | ggc | aac | 768 |
| Ala | Gln | Arg | Tyr | Ser | Phe | Val | Leu | Asn | Ala | Asn | Gln | Thr | Val | Gly | Asn | |
| | | | | 245 | | | | | 250 | | | | | 255 | | |

| | | | | | | | | | | | | | | | | |
|---|---|---|---|---|---|---|---|---|---|---|---|---|---|---|---|---|
| tac | tgg | gtc | cgc | gcg | aac | ccg | aac | ttc | gga | acg | gtt | ggg | ttc | gcc | ggg | 816 |
| Tyr | Trp | Val | Arg | Ala | Asn | Pro | Asn | Phe | Gly | Thr | Val | Gly | Phe | Ala | Gly | |
| | | | | 260 | | | | | 265 | | | | | 270 | | |

| | | | | | | | | | | | | | | | | |
|---|---|---|---|---|---|---|---|---|---|---|---|---|---|---|---|---|
| ggg | atc | aac | tcc | gcc | atc | ctg | cgc | tac | caa | ggc | gca | cca | gtc | gcc | gag | 864 |
| Gly | Ile | Asn | Ser | Ala | Ile | Leu | Arg | Tyr | Gln | Gly | Ala | Pro | Val | Ala | Glu | |
| | | 275 | | | | | 280 | | | | | 285 | | | | |

| | | | | | | | | | | | | | | | | |
|---|---|---|---|---|---|---|---|---|---|---|---|---|---|---|---|---|
| ccc | act | acg | acc | cag | acg | acg | tcg | gtg | atc | ccg | ctt | atc | gag | acg | aac | 912 |

```
            Pro Thr Thr Thr Gln Thr Thr Ser Val Ile Pro Leu Ile Glu Thr Asn
                290                 295                 300 ttg cac ccc ctc gct cgc atg cct gtg cct ggc agc ccg aca ccc ggg        960
Leu His Pro Leu Ala Arg Met Pro Val Pro Gly Ser Pro Thr Pro Gly
305                 310                 315                 320 ggc gtc gac aag gcg ctc aac ctc gcg ttt aac ttc aac ggc acc aac       1008
Gly Val Asp Lys Ala Leu Asn Leu Ala Phe Asn Phe Asn Gly Thr Asn
                325                 330                 335 ttc ttc atc aac aac gcg act ttc acg ccg ccg acc gtc ccg gta ctc       1056
Phe Phe Ile Asn Asn Ala Thr Phe Thr Pro Pro Thr Val Pro Val Leu
                340                 345                 350 ctc cag att ctg agc ggt gcg cag acc gca caa gac ctg ctc cct gca       1104
Leu Gln Ile Leu Ser Gly Ala Gln Thr Ala Gln Asp Leu Leu Pro Ala
                355                 360                 365 ggc tct gtc tac ccg ctc ccg gcc cac tcc acc atc gag atc acg ctg       1152
Gly Ser Val Tyr Pro Leu Pro Ala His Ser Thr Ile Glu Ile Thr Leu
            370                 375                 380 ccc gcg acc gcc ttg gcc ccg ggt gca ccg cac ccc ttc cac ctg cac       1200
Pro Ala Thr Ala Leu Ala Pro Gly Ala Pro His Pro Phe His Leu His
385                 390                 395                 400 ggt cac gcc ttc gcg gtc gtt cgc agc gcg ggg agc acc acg tat aac       1248
Gly His Ala Phe Ala Val Val Arg Ser Ala Gly Ser Thr Thr Tyr Asn
                405                 410                 415 tac aac gac ccg atc ttc cgc gac gtc gtg agc acg ggc acg ccc gcc       1296
Tyr Asn Asp Pro Ile Phe Arg Asp Val Val Ser Thr Gly Thr Pro Ala
                420                 425                 430 gcg ggc gac aac gtc acg atc cgc ttc cag acg gac aac ccc ggg ccg       1344
Ala Gly Asp Asn Val Thr Ile Arg Phe Gln Thr Asp Asn Pro Gly Pro
                435                 440                 445 tgg ttc ctc cac tgc cac atc gac ttc cac ctc gac gcg ggc ttc gcg       1392
Trp Phe Leu His Cys His Ile Asp Phe His Leu Asp Ala Gly Phe Ala
450                 455                 460 atc gtg ttc gca gag gac gtt gcg gac gtg aag gcg gcg aac ccg gtt       1440
Ile Val Phe Ala Glu Asp Val Ala Asp Val Lys Ala Ala Asn Pro Val
465                 470                 475                 480 ccg aag gcg tgg tcg gac ctg tgc ccg atc tac gac ggg ctg agc gag       1488
Pro Lys Ala Trp Ser Asp Leu Cys Pro Ile Tyr Asp Gly Leu Ser Glu
                485                 490                 495 gct aac cag tga                                                        1500
Ala Asn Gln <210> SEQ ID NO 2
<211> LENGTH: 499
<212> TYPE: PRT
<213> ORGANISM: Unknown Organism
<220> FEATURE:
<223> OTHER INFORMATION: Description of Unknown Organism: Laccase
      amino acid sequence

<400> SEQUENCE: 2

Ala Ile Gly Pro Val Ala Ser Leu Val Val Ala Asn Ala Pro Val Ser
1               5                   10                  15

Pro Asp Gly Phe Leu Arg Asp Ala Ile Val Val Asn Gly Val Val Pro
                20                  25                  30

Ser Pro Leu Ile Thr Gly Lys Lys Gly Asp Arg Phe Gln Leu Asn Val
            35                  40                  45

Val Asp Thr Leu Thr Asn His Ser Met Leu Lys Ser Thr Ser Ile His
        50                  55                  60

Trp His Gly Phe Phe Gln Ala Gly Thr Asn Trp Ala Asp Gly Pro Ala
65                  70                  75                  80
```

```
Phe Val Asn Gln Cys Pro Ile Ala Ser Gly His Ser Phe Leu Tyr Asp
                85                  90                  95

Phe His Val Pro Asp Gln Ala Gly Thr Phe Trp Tyr His Ser His Leu
            100                 105                 110

Ser Thr Gln Tyr Cys Asp Gly Leu Arg Gly Pro Phe Val Val Tyr Asp
            115                 120                 125

Pro Lys Asp Pro His Ala Ser Arg Tyr Asp Val Asp Asn Glu Ser Thr
            130                 135                 140

Val Ile Thr Leu Thr Asp Trp Tyr His Thr Ala Ala Arg Leu Gly Pro
145                 150                 155                 160

Arg Phe Pro Leu Gly Ala Asp Ala Thr Leu Ile Asn Gly Leu Gly Arg
                165                 170                 175

Ser Ala Ser Thr Pro Thr Ala Ala Leu Ala Val Ile Asn Val Gln His
            180                 185                 190

Gly Lys Arg Tyr Arg Phe Arg Leu Val Ser Ile Ser Cys Asp Pro Asn
            195                 200                 205

Tyr Thr Phe Ser Ile Asp Gly His Asn Leu Thr Val Ile Glu Val Asp
            210                 215                 220

Gly Ile Asn Ser Gln Pro Leu Leu Val Asp Ser Ile Gln Ile Phe Ala
225                 230                 235                 240

Ala Gln Arg Tyr Ser Phe Val Leu Asn Ala Asn Gln Thr Val Gly Asn
                245                 250                 255

Tyr Trp Val Arg Ala Asn Pro Asn Phe Gly Thr Val Gly Phe Ala Gly
                260                 265                 270

Gly Ile Asn Ser Ala Ile Leu Arg Tyr Gln Gly Ala Pro Val Ala Glu
            275                 280                 285

Pro Thr Thr Thr Gln Thr Thr Ser Val Ile Pro Leu Ile Glu Thr Asn
            290                 295                 300

Leu His Pro Leu Ala Arg Met Pro Val Pro Gly Ser Pro Thr Pro Gly
305                 310                 315                 320

Gly Val Asp Lys Ala Leu Asn Leu Ala Phe Asn Phe Asn Gly Thr Asn
                325                 330                 335

Phe Phe Ile Asn Asn Ala Thr Phe Thr Pro Pro Thr Val Pro Val Leu
            340                 345                 350

Leu Gln Ile Leu Ser Gly Ala Gln Thr Ala Gln Asp Leu Leu Pro Ala
            355                 360                 365

Gly Ser Val Tyr Pro Leu Pro Ala His Ser Thr Ile Glu Ile Thr Leu
            370                 375                 380

Pro Ala Thr Ala Leu Ala Pro Gly Ala Pro His Pro Phe His Leu His
385                 390                 395                 400

Gly His Ala Phe Ala Val Val Arg Ser Ala Gly Ser Thr Thr Tyr Asn
                405                 410                 415

Tyr Asn Asp Pro Ile Phe Arg Asp Val Val Ser Thr Gly Thr Pro Ala
            420                 425                 430

Ala Gly Asp Asn Val Thr Ile Arg Phe Gln Thr Asp Asn Pro Gly Pro
            435                 440                 445

Trp Phe Leu His Cys His Ile Asp Phe His Leu Asp Ala Gly Phe Ala
            450                 455                 460

Ile Val Phe Ala Glu Asp Val Ala Asp Val Lys Ala Ala Asn Pro Val
465                 470                 475                 480

Pro Lys Ala Trp Ser Asp Leu Cys Pro Ile Tyr Asp Gly Leu Ser Glu
                485                 490                 495
```

Ala Asn Gln

<210> SEQ ID NO 3
<211> LENGTH: 162
<212> TYPE: DNA
<213> ORGANISM: Unknown Organism
<220> FEATURE:
<223> OTHER INFORMATION: Description of Unknown Organism: Brazzein
      nucleotide sequence

<400> SEQUENCE: 3
caggacaagt gcaagaaggt gtacgagaac tacccggtgt ccaagtgcca gctcgccaac      60
cagtgcaact acgactgcaa gctcgacaag cacgcccgct ccggcgagtg cttctacgac    120
gagaagcgca acttccagtg catctgcgac tactgcgagt ac                       162

<210> SEQ ID NO 4
<211> LENGTH: 174
<212> TYPE: DNA
<213> ORGANISM: Unknown Organism
<220> FEATURE:
<223> OTHER INFORMATION: Description of Unknown Organism: Aprotinin
      nucleotide sequence

<400> SEQUENCE: 4
cgcccggact tctgcctcga gccgccatac accggaccct gcaaggccag gatcatccgc      60
tacttctaca cgccaaggc cggcctctgc cagaccttcg tttacggagg ctgccgcgcc     120
aagcgcaaca acttcaagag cgctgaggac tgcatgcgca cctgcggagg cgcc          174

<210> SEQ ID NO 5
<211> LENGTH: 1077
<212> TYPE: DNA
<213> ORGANISM: Phanerochaete chrysosporium
<220> FEATURE:
<221> NAME/KEY: CDS
<222> LOCATION: (1)..(1077)

<400> SEQUENCE: 5

```
gca gtc tgt cca gac ggt acc cgc gtc acc aac gcg gcg tgc tgc gct      48
Ala Val Cys Pro Asp Gly Thr Arg Val Thr Asn Ala Ala Cys Cys Ala
 1               5                  10                  15 ttc att ccg ctc gca cag gac ttg caa gag act ctg ttc cag ggt gac      96
Phe Ile Pro Leu Ala Gln Asp Leu Gln Glu Thr Leu Phe Gln Gly Asp
             20                  25                  30 tgt ggc gaa gat gcc cac gaa gtc atc cgt ctg acc ttc cac gac gct     144
Cys Gly Glu Asp Ala His Glu Val Ile Arg Leu Thr Phe His Asp Ala
         35                  40                  45 att gca atc tcc cag agc cta ggt cct cag gct ggc ggc ggt gct gac     192
Ile Ala Ile Ser Gln Ser Leu Gly Pro Gln Ala Gly Gly Gly Ala Asp
     50                  55                  60 ggc tcc atg ctg cac ttc ccg aca atc gag ccc aac ttc tcc gcc aac     240
Gly Ser Met Leu His Phe Pro Thr Ile Glu Pro Asn Phe Ser Ala Asn
 65                  70                  75                  80 aac ggc atc gat gac tcc gtc aac aac ttg ctt ccc ttc atg cag aaa     288
Asn Gly Ile Asp Asp Ser Val Asn Asn Leu Leu Pro Phe Met Gln Lys
                 85                  90                  95 cac gac acc atc agt gcc gcc gat ctt gta cag ttc gcc ggt gcg gtc     336
His Asp Thr Ile Ser Ala Ala Asp Leu Val Gln Phe Ala Gly Ala Val
            100                 105                 110 gcg ctg agc aac tgc cca ggt gct cct cgc ctc gag ttc atg gct gga     384
Ala Leu Ser Asn Cys Pro Gly Ala Pro Arg Leu Glu Phe Met Ala Gly
        115                 120                 125
```

```
cgt ccg aac act acc atc ccc gca gtt gag ggc ctc att cct gag cct    432
Arg Pro Asn Thr Thr Ile Pro Ala Val Glu Gly Leu Ile Pro Glu Pro
    130                 135                 140 caa gac agc gtc acc aaa atc ctg cag cgc ttc gag gac gcc ggc aac    480
Gln Asp Ser Val Thr Lys Ile Leu Gln Arg Phe Glu Asp Ala Gly Asn
145                 150                 155                 160 ttc tcg ccg ttc gag gtc gtc tcg ctc ctg gct tca cac acc gtt gct    528
Phe Ser Pro Phe Glu Val Val Ser Leu Leu Ala Ser His Thr Val Ala
                165                 170                 175 cgt gcg gac aag gtc gac gag acc atc gat gct gcg ccc ttc gac tcg    576
Arg Ala Asp Lys Val Asp Glu Thr Ile Asp Ala Ala Pro Phe Asp Ser
            180                 185                 190 aca ccc ttc acc ttc gac acc cag gtg ttc ctc gag gtc ctg ctc aag    624
Thr Pro Phe Thr Phe Asp Thr Gln Val Phe Leu Glu Val Leu Leu Lys
        195                 200                 205 ggc aca ggc ttc ccg ggc tcg aac aac aac acc ggc gag gtg atg tcg    672
Gly Thr Gly Phe Pro Gly Ser Asn Asn Asn Thr Gly Glu Val Met Ser
    210                 215                 220 ccg ctc cca ctc ggc agc ggc agc gac acg ggc gag atg cgc ctg cag    720
Pro Leu Pro Leu Gly Ser Gly Ser Asp Thr Gly Glu Met Arg Leu Gln
225                 230                 235                 240 tcc gac ttt gcg ctc gcg cgc gac gag cgc acg gcg tgc ttc tgg cag    768
Ser Asp Phe Ala Leu Ala Arg Asp Glu Arg Thr Ala Cys Phe Trp Gln
                245                 250                 255 tcg ttc gtc aac gag cag gag ttc atg gcg gcg agc ttc aag gcc gcg    816
Ser Phe Val Asn Glu Gln Glu Phe Met Ala Ala Ser Phe Lys Ala Ala
                260                 265                 270 atg gcg aag ctc gcg atc ctc ggc cac agc cgc agc agc ctc atc gac    864
Met Ala Lys Leu Ala Ile Leu Gly His Ser Arg Ser Ser Leu Ile Asp
            275                 280                 285 tgc agc gac gtc gtc ccc gtc ccg aag ccc gcc gtc aac aag ccc gcg    912
Cys Ser Asp Val Val Pro Val Pro Lys Pro Ala Val Asn Lys Pro Ala
        290                 295                 300 acg ttc ccc gcg acg aag ggc ccc aag gat ctc gac aca ctc acg tgc    960
Thr Phe Pro Ala Thr Lys Gly Pro Lys Asp Leu Asp Thr Leu Thr Cys
305                 310                 315                 320 aag gcc ctc aag ttc ccg acg ctg acc tct gac ccc ggt gct acc gag   1008
Lys Ala Leu Lys Phe Pro Thr Leu Thr Ser Asp Pro Gly Ala Thr Glu
                325                 330                 335 acc ctc atc ccc cac tgc tcc aac ggc ggc atg tcc tgc cct ggt gtt   1056
Thr Leu Ile Pro His Cys Ser Asn Gly Gly Met Ser Cys Pro Gly Val
            340                 345                 350 cag ttc gat ggc cct gcc tga                                        1077
Gln Phe Asp Gly Pro Ala
        355
```

<210> SEQ ID NO 6
<211> LENGTH: 358
<212> TYPE: PRT
<213> ORGANISM: Phanerochaete chrysosporium

<400> SEQUENCE: 6

```
Ala Val Cys Pro Asp Gly Thr Arg Val Thr Asn Ala Ala Cys Cys Ala
1               5                   10                  15

Phe Ile Pro Leu Ala Gln Asp Leu Gln Glu Thr Leu Phe Gln Gly Asp
                20                  25                  30

Cys Gly Glu Asp Ala His Glu Val Ile Arg Leu Thr Phe His Asp Ala
            35                  40                  45

Ile Ala Ile Ser Gln Ser Leu Gly Pro Gln Ala Gly Gly Gly Ala Asp
        50                  55                  60
```

```
Gly Ser Met Leu His Phe Pro Thr Ile Glu Pro Asn Phe Ser Ala Asn
 65                  70                  75                  80

Asn Gly Ile Asp Asp Ser Val Asn Asn Leu Leu Pro Phe Met Gln Lys
             85                  90                  95

His Asp Thr Ile Ser Ala Ala Asp Leu Val Gln Phe Ala Gly Ala Val
            100                 105                 110

Ala Leu Ser Asn Cys Pro Gly Ala Pro Arg Leu Glu Phe Met Ala Gly
        115                 120                 125

Arg Pro Asn Thr Thr Ile Pro Ala Val Glu Gly Leu Ile Pro Glu Pro
130                 135                 140

Gln Asp Ser Val Thr Lys Ile Leu Gln Arg Phe Glu Asp Ala Gly Asn
145                 150                 155                 160

Phe Ser Pro Phe Glu Val Val Ser Leu Leu Ala Ser His Thr Val Ala
                165                 170                 175

Arg Ala Asp Lys Val Asp Glu Thr Ile Asp Ala Ala Pro Phe Asp Ser
            180                 185                 190

Thr Pro Phe Thr Phe Asp Thr Gln Val Phe Leu Glu Val Leu Leu Lys
        195                 200                 205

Gly Thr Gly Phe Pro Gly Ser Asn Asn Asn Thr Gly Glu Val Met Ser
210                 215                 220

Pro Leu Pro Leu Gly Ser Gly Ser Asp Thr Gly Glu Met Arg Leu Gln
225                 230                 235                 240

Ser Asp Phe Ala Leu Ala Arg Asp Glu Arg Thr Ala Cys Phe Trp Gln
                245                 250                 255

Ser Phe Val Asn Glu Gln Glu Phe Met Ala Ala Ser Phe Lys Ala Ala
            260                 265                 270

Met Ala Lys Leu Ala Ile Leu Gly His Ser Arg Ser Ser Leu Ile Asp
        275                 280                 285

Cys Ser Asp Val Val Pro Val Pro Lys Pro Ala Val Asn Lys Pro Ala
290                 295                 300

Thr Phe Pro Ala Thr Lys Gly Pro Lys Asp Leu Asp Thr Leu Thr Cys
305                 310                 315                 320

Lys Ala Leu Lys Phe Pro Thr Leu Thr Ser Asp Pro Gly Ala Thr Glu
                325                 330                 335

Thr Leu Ile Pro His Cys Ser Asn Gly Gly Met Ser Cys Pro Gly Val
            340                 345                 350

Gln Phe Asp Gly Pro Ala
        355

<210> SEQ ID NO 7
<211> LENGTH: 1976
<212> TYPE: DNA
<213> ORGANISM: Artificial Sequence
<220> FEATURE:
<223> OTHER INFORMATION: Description of Artificial Sequence: Synthetic
      modified ubiquitin-like promoter

<400> SEQUENCE: 7
gtgcagcgtg acccggtcgt gcccctctct agagataatg agcattgcat gtctaagtta      60
taaaaaatta ccacatattt tttttgtcac acttgtttga agtgcagttt atctatcttt     120
atacatatat ttaaacttta ctctacgaat aatataatct atagtactac aataatatca     180
gtgttttaga gaatcatata aatgaacagt tagacatggt ctaaaggaca attgagtatt     240
ttgacaacag gactctacag ttttatcttt ttagtgtgca tgtgttctcc ttttttttg     300
```

-continued

```
caaatagctt cacctatata atacttcatc cattttatta gtacatccat ttagggttta    360
gggttaatgg ttttttataga ctaattttttt tagtacatct attttattct attttagcct    420
ctaaattaag aaaactaaaa ctctatttta gttttttttat ttaataattt agatataaaa    480
tagaataaaa taaagtgact aaaaattaaa caaatacccct ttaagaaatt aaaaaaacta    540
aggaaacatt tttcttgttt cgagtagata atgccagcct gttaaacgcc gtcgacgagt    600
ctaacggaca ccaaccagcg aaccagcagc gtcgcgtcgg gccaagcgaa gcagacggca    660
cggcatctct gtcgctgcct ctcgagagtt ccgctccacc gttggacttg ctccgctgtc    720
ggcatccaga aattgcgtgg cggagcggca gacgtgagcc ggcacggcag gcggcctcct    780
cctcctctca cggcacggca gctacggggg attccttttcc caccgctcct tcgctttccc    840
ttcctcgccc gccgtaataa atagacaccc cctccacacc ctctttcccc aacctcgtgt    900
tgttcggagc gcacacacac acaaccagat ctcccccaaa tccacccgtc ggcacctccg    960
cttcaaggta cgccgctcgt cctccccccc ccccctctc taccttctct agatcggcgt   1020
tccggtccat ggttagggcc cggtagttct acttctgttc atgtttgtgt tagatccgtg   1080
tttgtgttag atccgtgctg ctagcgttcg tacacggatg cgacctgtac gtcagacacg   1140
ttctgattgc taacttgcca gtgtttctct ttggggaatc ctgggatggc tctagccgtt   1200
ccgcagacgg gatcgatttc atgatttttt ttgtttcgtt gcatagggtt tggtttgccc   1260 ttttcccttta tttcaatata tgccgtgcac ttgtttgtcg ggtcatcttt tcatgctttt   1320
ttttgtcttg gttgtgatga tgtggtctgg ttgggcggtc gttctagatc ggagtagaat   1380
tctgtttcaa actacctggt ggatttattta atttttggatc tgtatgtgtg tgccatacat   1440
attcatagtt acgaattgaa gatgatggat ggaaatatcg atctaggata ggtatacatg   1500
ttgatgcggg ttttactgat gcatatacag agatgctttt tgttcgcttg gttgtgatga   1560
tgtggtgtgg ttgggcggtc gttcattcgt tctagatcgg agtagaatac tgtttcaaac   1620
tacctggtgt atttattaat tttggaactg tatgtgtgtg tcatacatct tcatagttac   1680
gagtttaaga tggatggaaa tatcgatcta ggataggtat acatgttgat gtgggtttta   1740
ctgatgcata tacatgatgg catatgcagc atcattcat atgctctaac cttgagtacc   1800
tatctattat aataaacaag tatgttttat aattattttg atcttgatat acttggatga   1860
tggcatatgc agcagctata tgtggatttt tttagccctg ccttcatacg ctatttattt   1920
gcttggtact gtttcttttg tcgatgctca ccctgttgtt tggtgttact tctgca      1976
```

```
<210> SEQ ID NO 8
<211> LENGTH: 4
<212> TYPE: PRT
<213> ORGANISM: Artificial Sequence
<220> FEATURE:
<223> OTHER INFORMATION: Description of Artificial Sequence:
      Illustrative peptide motif

<400> SEQUENCE: 8

Lys Asp Glu Leu
  1
```

METHOD OF INCREASING EXPRESSION OF HETEROLOGOUS PROTEINS IN PLANTS

REFERENCE TO RELATED APPLICATIONS

This application claims benefit of U.S. provisional application Ser. No. 60/324,308, filed Sep. 24, 2001. The contents of this application are incorporated herein by reference.

BACKGROUND OF THE INVENTION

The production of heterologous proteins in plants for various purposes is a fast-growing field of study. Plants as biofactories for the production of proteins is a new technology that is being employed by a number of groups for edible vaccines, pharmaceuticals and industrial enzymes. Hood, E. and Howard, J. Protein Products from Heterologous Plants. *Agro-Food-Industry Hi-Tech,* 3, Vol. 10, May/June 1999, pp. 35-36 Hood, E. and Jilka, J. (1999) Plant Based Production of Xenogenic Proteins. *Current Opinion in Biotechnology,* 10:4, pp. 382-386. Pharmaceutical and vaccine production in plants has several advantages in that the material contains no contaminating organisms and can be directly consumed. Production of industrial enzymes in plants provides the possibility of considerably reduced production costs, the benefit of recovered costs through sale of by products, easier transportation and reduced chance of contamination.

Over-expression of a protein in a heterologous plant requires quite high expression levels to make the system economically viable, a condition that has been achieved for a number of proteins, e.g. the diagnostic protein, avidin (U.S. Pat. No. 5,767,379); aprotinin (U.S. Pat. No. 5,824,870); hepatitis vaccine (U.S. Pat. No. 5,914,123); Transmissible Gastroenteritis vaccine (U.S. Pat. No. 6,034,298); viral vaccines (U.S. Pat. No. 6,136,320); proteases (U.S. Pat. No. 6,087,558) and laccase (WO 00/20615). Using plants as biofactories for pharmaceutical and industrial enzyme production provides considerable advantages over traditional methods of such protein production, since plants provide easier transport and cost savings, but also can be far more readily produced in large quantities than when produced in bacteria or fungi for example, allowing for even further increases in the amount of enzyme which may be produced.

Achieving high levels of enzyme production in plants is impacted by several factors, such as location of expression of the protein within specific tissues and within particular subcellular compartments to insulate the plant tissues from the activity of the protein. Thus, in WO 00/20615, it is discussed that preferentially directing expression to the seed of the plant and also to plant cell wall tissue and to the endoplasmic reticulum of the plant cell is advantageous in increasing protein production. Attempts continue to yet further increase expression levels of the heterologous proteins in plants to provide optimum efficiency, efficacy and decrease costs.

When choosing a variety of plant in which to introduce a heterologous nucleotide sequence in order to express a heterologous protein, two approaches have been typical. One is to select those varieties or lines that have good agronomic traits. These so-called "elite" plants primarily demonstrate high yield. They also may have traits that make them better able to withstand adverse weather conditions in the area in which they are grown, or withstand disease or insect attack better than other plants. If the output of grain can be increased, it is believed, the amount of heterologous protein produced will be increased. Indeed, this can be a successful approach. As a result, there is little incentive to select non-elite plants that demonstrate poor agronomic traits.

Another approach which has been used in selecting plants for heterologous protein production is to choose a plant which has a protein sink, that is, where one or more of the plant proteins is reduced as compared with the naturally occurring wild-type version of the variety or line. In this approach, a promoter, which directs the heterologous protein expression to the area of the sink, or protein depletion, is expected to provide for increased expression levels of the heterologous protein. For example, in one study, Takaiwa used rice plants with reduced glutelin levels in the endosperm to express heterologous protein. This rice had reduced glutelin levels, and is not a rice with reduced levels of alcohol soluble proteins. A nucleotide sequence expressing the desired protein was linked to an endosperm promoter and introduced into the plants. Takaiwa, F. "Development of high accumulation systems in rice endosperm" Abstract, New Frontier of Plant Molecular Farming; NIAR, Tsukuba City Japan, Mar. 7-8, 2000. The result, as expected, was increased expression levels of the heterologous protein in the endosperm.

The inventors have surprisingly found that one can obtain more plants with higher expression levels of heterologous protein by selecting host plants in a manner contrary to what is known about plant expression systems. They have found that if a plant is selected which has reduced alcohol-soluble protein levels in the endosperm, significantly higher expression levels of heterologous protein are achieved in the embryo. Expression levels of two to three times that in plants which do not have reduced alcohol soluble levels are obtained. Thus, a sink is created in one part of the plant tissue, but protein levels actually increase elsewhere. Impacting the endosperm causes increased levels of heterologous protein accumulation in the embryo.

Normally, plants with reduced alcohol-soluble protein levels, the opaque mutants for example, have decreased protein levels in the endosperm and the embryo has increased levels of saline-soluble water-insoluble proteins, such as globulins. Puckett, J. L. and Kriz, A. L. "Globulin Gene Expression in Opaque-2 and Floury-2 Mutant Maize Embryos" *Maydica* (1991) 36:161-167. (see p. 162). However, the inventors have found that the amount of heterologous protein is increased considerably in such plants. It is especially surprising when heterologous water-soluble proteins are introduced into the plant, the levels of such heterologous protein production are increased, even though there has been an increase in the embryo of native water-insoluble proteins. Not only is the sink "filled" elsewhere, but it is filled with a non-native protein, and can be filled with a non-native protein that is quite different from that which is depleted.

The inventors have discovered that by introducing nucleotide sequences encoding heterologous protein into plants that have reduced levels of alcohol soluble proteins in the endosperm, there is an increase in the expression level of the heterologous protein. This is unexpected for several reasons. First, the literature indicates protein levels decrease in such plants. Second, if the sink created was to be filled, one would expect native plant protein to fill the sink, not heterologous protein. Third, the sink is created by reduction of alcohol-soluble proteins in the endosperm but the heterologous protein is increased as measured in nanograms of protein per milligram of dry weight of plant seed. Also, the zein content of the seed is only about 8% of the seed weight. In plants having reduced zein content, the amount can be decreased by 30% to 90%. However, the increases obtained in heterologous expression are two to three times that of expression in a plant not having reduced alcohol soluble proteins in the endosperm. Finally, the levels of heterologous soluble protein expression are particularly high in the embryo of the seed of the opaque plant, which is surprising given that water insoluble proteins increase in the embryo as noted by Puckett, supra.

Without wishing to be bound by any theory, it is believed that when there are reduced proteins in the endosperm, somehow the plant "responds" to the heterologous protein as a globulin-like protein and fills the embryo, even to the exclusion of native globulins, and even though the heterologous protein is water-soluble, not water-insoluble, as globulins are. Ranges of expression are recovered, and the levels of expression are overall higher using these plant backgrounds.

The inventors have found that plants with reduced levels of alcohol soluble protein levels in the endosperm provide a good host in which to express heterologous proteins. It is particularly surprising to use this type of plant, since it typically shows such poor agronomic traits. For example, the opaque mutants have been studied in the past as a potential source of germplasm to increase lysine content and nutrition in corn, but were found to have low yield and susceptibility to disease. Seed of the plant exhibit a soft, chalky, non-transparent appearance, with very little hard vitreous or horny endosperm. Hence, the name opaque was applied to such mutants. Because of these characteristics, they are more prone to damage by seed rot, insects, rodents and harvesting damage. In fact, it has been stated that "[d]ue to the reduction in seed weight and total protein content, the double mutant has no practical interest in breeding maize for quality." Salamini, et al, "Mucronate, Mc, a dominant gene of maize which interacts with opaque-2 to suppress zein synthesis" *Theor. Appl. Genet.* (1983) 65:123-128. Here, however, the inventors have found an advantage in selecting for such plants as a source of heterologous protein.

In addition, the inventors have also found that high oil plants are a desirable choice of plant host for expressing heterologous protein.

High-oil content plants have been studied for some time for their improved nutritional value as animal grain. For example, maize is an important cereal crop used for livestock feeding, commercial products and human consumption. Increasing oil content adds value to such products. Much of the work involving high-oil plants has been devoted to increasing yield while retaining the high-oil content trait. See e.g., Alexander, *Maydica* 44 (1999)222-112. High-oil hybrids with greater than 6% by dry weight oil content are lower in yield than hybrids with lower levels of oil. These plants, such as corn, have been transformed with heterologous nucleotide sequences, such as in Asrar, U.S. Pat. No. 6,091,002 in which polyhydroxyalkanoate (PHA) polymers are produced in high oil plants since these plants produce carbon substrates which can be employed for PHA biosynthesis. Reports on whether there is increased protein content correlated with high oil phenotype have varied. See, for example, Kovacs-Schneider et al. *Novenytermeles* 35 (1986): 383-389 in which they discuss selection for high oil content in corn correlated with a simultaneous increase in protein content attributed to an increase in embryo size. In soybeans, it has been noted that protein increases insignificantly in high oil types. Qiu, L. et al., *Scientia Agricultura Sinica* (1990) 23, No. 5: 28-32. In cotton, there is a negative correlation of protein content with seed oil. Zhou, Z. G., et al. Shaanxi *Journal of Ag. Sci.* (1992) 3: 3-5. Thus statements regarding protein content in high oil plants have been highly contradictory.

Regardless of whether or not high oil plants are correlated with high protein, the inventors have found that not all plants with higher protein content are acceptable hosts for production of heterologous protein. The Illinois High Protein variety, for example, is, as its name implies, a hybrid with increased protein levels in the seed. However, the inventors have found that it is not a good host, and that heterologous protein levels are quite low using this plant. However, if high oil plants are the host for heterologous protein expression, heterologous protein levels are significantly increased. Further, the heterologous protein is apparently out-competing the native protein already present in the embryo. High oil plants do not have a "sink" as with the low alcohol soluble protein plants discussed above. In this situation, the heterologous protein increases rather than native protein acting to limit heterologous protein expression.

In addition, the inventors have found that when the heterologous protein is introduced into a cross combining the high oil and opaque plants, yet further increases in heterologous protein expression are achieved.

SUMMARY OF THE INVENTION

The invention relates to the discovery that expression of heterologous proteins in a pool of plants can be increased by expressing the protein in plants having reduced levels of alcohol-soluble proteins, in high oil plants, and in plants that are a cross of the two.

An object of the invention is to increase expression of heterologous protein in a pool of plants by introducing a nucleotide sequence encoding the protein into plants having reduced levels of alcohol-soluble proteins in the endosperm and selecting for high expressing plants in the progeny recovered.

An object of the invention is to increase expression of a heterologous water-soluble protein in the seed of a plant comprising introducing a nucleotide sequence encoding the heterologous protein into plants which have reduced levels of alcohol soluble proteins in the endosperm.

Still another object of the invention is to increase expression of a heterologous protein in the seed of a plant comprising introducing the nucleotide sequence encoding the protein into opaque plants.

Another object of the invention is to increase expression of heterologous protein in a plant by introducing a nucleotide sequence encoding the protein into high oil plants.

A still further object of the invention is to increase expression of heterologous protein in a plant by introducing a nucleotide sequence encoding the protein into a cross between high oil plants and plants having reduced levels of alcohol-soluble proteins in the endosperm.

Yet another object of the invention is to introduce the nucleotide sequence encoding the protein into the plants by direct transformation into the plants or in a preferred method, direct transformation is used to introduce the sequence into a first plant, which is then crossed with a second plant. In a more preferred method, the nucleotide sequence is transformed into the first plant, then in a first cross, crossed with one of the high oil plant or plant with reduced levels of alcohol-soluble proteins in the endosperm to produce progeny, the progeny then crossed with either the high oil plant or plant with reduced levels of alcohol soluble proteins in the endosperm, whichever was not used in the first cross.

Yet another object of the invention is the increase of expression of a heterologous protein in a plant by introducing a nucleotide sequence encoding the protein in a monocot or dicot plant that either has reduced alcohol soluble protein levels in the endosperm, are high oil plants, or both.

BRIEF DESCRIPTION OF THE DRAWINGS

FIGS. 2A, B and C is the nucleotide sequence of a laccase gene and the amino acid sequence encoded thereby (SEQ ID NOs:1 and 2).

FIGS. 14A and B sets forth a nucleotide sequence encoding manganese peroxidase and the amino acid sequence encoded thereby. (SEQ ID NO:5 and 6)

FIG. 16 is a graph showing expression of manganese peroxidase protein measured in nanograms of manganese peroxidase per milligram of dry weight of seed, where expressed in elite (shaded bars) or high oil (unshaded bars) plants. The measurements were taken from seeds from single ears.

DETAILED DESCRIPTION OF THE PREFERRED EMBODIMENT

Figure 1:
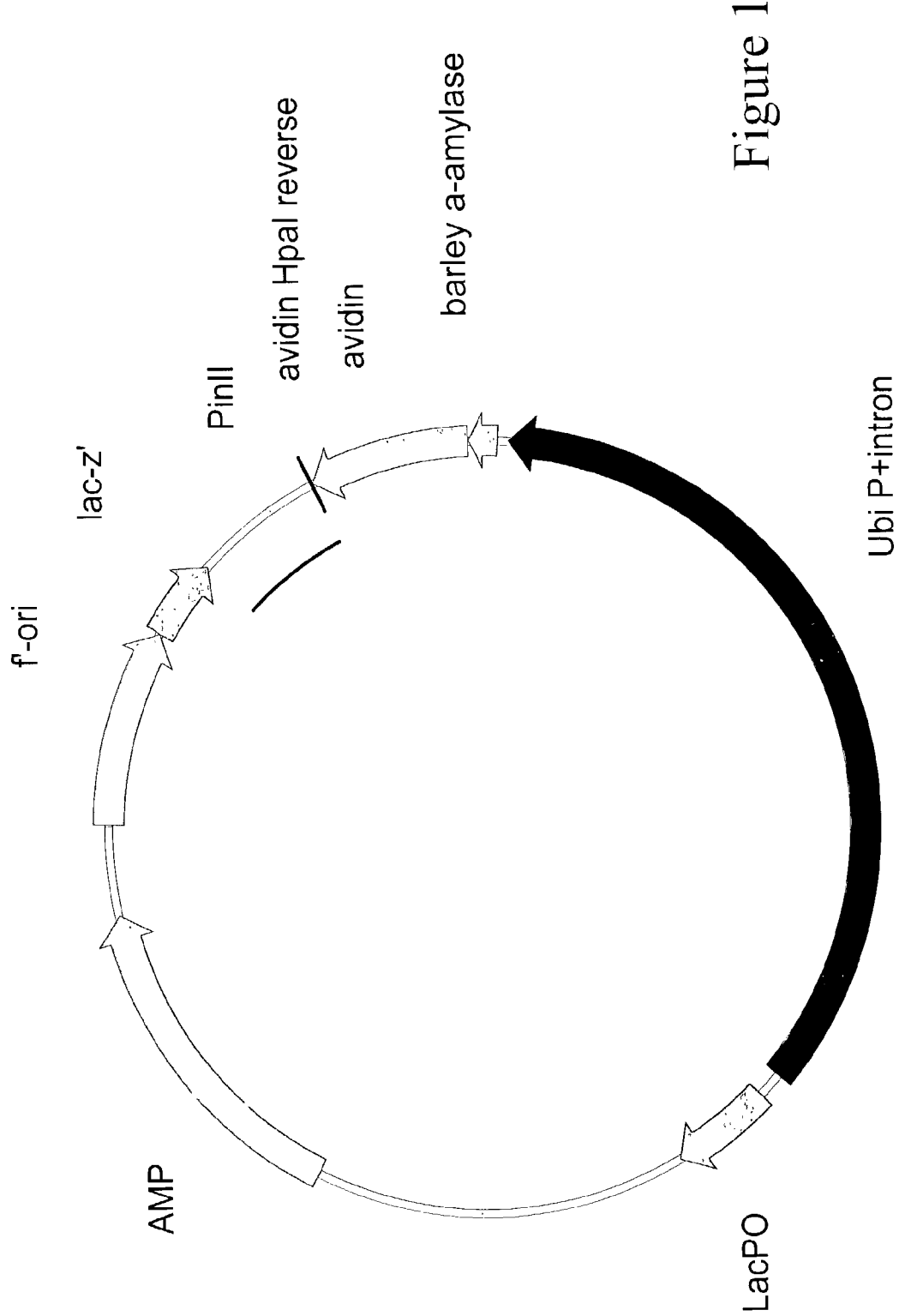
FIG. 1 shows the plasmid PHP 5168 used to introduce sequences encoding the avidin protein in plants.

The following includes description of the preferred embodiments of the invention and the examples set forth below are not intended to limit the scope of the invention, but are illustrative in nature. All references cited are incorporated herein by reference.

The inventors have found that expression of a heterologous protein in plants with reduced levels of alcohol soluble proteins in the endosperm and/or high oil plants results in an increase in expression of the heterologous protein in the seed of the plant. The expression is particularly increased in the embryo of the plant.

The present invention relates to any plants having reduced levels of alcohol soluble proteins in the endosperm when compared to the commercial commodity feed plant. In corn, for example, yellow dent number 2 is a variety that is an example of a common commercial feed plant. In rice, Japonica or Indica are common commercial varieties. The "OHS endosperm mutants" (to refer to this type of plants using an abbreviated term) are found in a variety of plant species. These OHS endosperm mutants may have reduced levels of zeins, gliadin, glutenin, hordein, prolamins, avenins or any of a variety of alcohol soluble proteins. The table below lists (without intending to be limiting) several examples of these mutants.

TABLE 1

| Grain species | % DW as protein | % protein as alcohol soluble protein | Protein common name | Mutants | Reference |
|---|---|---|---|---|---|
| Maize | 8-10 | 70 | Zein | Opaque mucronate floury | Coleman & Larkins, (1999) Seed Proteins, Shewry and Casey, eds., Kluwer Acad. Pub., Dordrecht, The Netherlands pp. 109-139 |
| Barley | 10 | 50 | Hordein | Risø | Doll, (1999) Seed Proteins, supra, pp. 207-223 |
| Rice | 8 | 10-20 | — | Opaque | Kaushik et al 1991 Theor. Appl. Genet. Vol. 83, No. 2 p. 146-152 |
| Sorghum | 10 | 50 | Kafirin | High lysine (floury) | Ejeta, G. & Aztell, J. Cereal Chemistry (1987) 3:137-139 |

Opaque plants are one example of OHS endosperm mutant plants. When the homozygous alleles responsible for the trait are present, a phenotype called "opaque" results, because the normally vitreous, hard endosperm changes to a soft powdery endosperm which is opaque in appearance. This results from reduction of alcohol-soluble proteins and the increased accumulation of other endosperm proteins. Further, as noted above, the embryos of these plants show an increase in water-insoluble proteins, the globulins.

By way of further example, Zea mays L., corn, demonstrates opaque phenotype associated with mutations identified by their locus on the chromosome map. A sample of such mutants and their protein characteristics is listed in Table 2 below.

TABLE 2

| Locus | Chromosomal location | Inheritance | % Zein inhibition | Zein subunits affected |
|---|---|---|---|---|
| Opaque 2 (o2) | Chr. 7, short arm | Recessive | 47.0 | Mainly 22 kD |
| Opaque 6 (o6) |  | Recessive | 88.5 | All subunits |
| Opaque 7 (o7) | Chr. 10, long arm | Recessive | 77.5 | Mainly 20 kD |

TABLE 2-continued

| Locus | Chromosomal location | Inheritance | % Zein inhibition | Zein subunits affected |
|---|---|---|---|---|
| Floury 2 (fl2) | Chr. 4, short arm | Semidominant | 34.6 | All subunits |
| Mucronate (Mc) | | Dominant | 29.0 | All subunits |

As can be seen from the summary above, these mutants typically are defective in some manner and not typically used in commercial production.

In maize, zeins are the alcohol-soluble proteins that are reduced in the endosperm. There are three categories of zeins in endosperm: α zeins, which represent 75 to 85% of the total zein content in the seed and have a molecular weight of about 19 to 22 kD; β zeins representing 10 to 15% of the total zein content and having a molecular weight of about 14 kD; and γ zeins which represent about 5 to 10% of the total zein content in the seed and having a molecular weight of 16 or 27 kD.

The zeins account for only 8% of the weight of the seed. In plants having reduced zein content, the amount can be decreased by 30% to 90%. Despite the fact it accounts for such a small percentage of the seed, the inventors have found expression of the heterologous proteins increases two to three times over that in non-opaque plants. Further, these water-soluble proteins are expressed at high levels even though the reduction in proteins in the mutants is of proteins that are alcohol soluble/water insoluble.

High oil plants are those in which the oil content of the seed is higher than lower oil producing plants (hybrid #2 yellow dent corn). High oil seed is that which contains elevated levels of oil on a percent dry weight basis when compared to low-oil seeds. High oil plants and their production are well known. The invention will be applicable to any one of plants in which high oil levels may be produced over that occurring in the native, or wild type plant. Examples of plants that have high oil producing varieties include, but are not limited to corn, soybeans, sorghum, wheat, rye, triticale, rice, barley, oats, flax, safflower, canola, sunflower and the various millet genera.

Plant breeders have attempted over time to study and increase oil content of feed plants. Representative discussions can be found at U.S. Pat. No. 6,232,529 discussing increasing oil in soybeans, sunflower, cottonseed and canola; at U.S. Pat. No. 6,063,424 on high oil rice. High oil corn plants and their production are discussed at length in the patent to Bergquist et al, U.S. Pat. No. 5,706,603 and at Alexander, D. E. (1999). *Short Communications*. 44: 111-112. High oil corn is a commercially desirable value-added product in the animal feed industry. Low-Oil Corn seed are those which contain oil in the range of about 2.5-5.1 percent on a dry weight basis. This level of oil is typical of a wide range of field corn inbreds and hybrids.

Perhaps the most thoroughly studied high-oil corn populations are the Illinois High Oil (IHO) and Alexander High Oil (Alexho) populations developed at the University of Illinois. IHO was developed by modified mass selection within the open pollinated corn variety, Burr's White, over more than 80 cycles of selection commencing in 1896 (Alexander, D. E., (1988) Proceedings of the 43rd Annual Corn and Sorghum Industrial Research Conference, pp. 97-105; Dudley, J. W., et al., (1974) Crop Science Society of America, Madison, Wis., J. W. Dudley, ed pp. 181-212). The highest average kernel or grain oil content achieved in this population is about 22% oil on a dry weight basis. Dr. Denton Alexander, employing both mass and single kernel selection within a synthetic population (Alexho), was able to achieve an average oil content of approximately 22% following 28 cycles of selection (Alexander, D. E., (1988) Proceedings of the 43rd Annual Corn and Sorghum Industrial Research Conference, pp. 97-105). A number of corn inbreds have been released from the IHO (R802A) and Alexho (R805, R806) populations and are available to the public through the Director of Agricultural Experiment Station, University of Illinois, Urbana, Ill.

As noted, one would expect that with the larger embryo associated with high oil corn, and reports of increased protein content, that native protein levels would increase, in competition with heterologous protein production. However, this has not been found to be true; the heterologous protein increases, both on a percent of total protein, and on a weight basis.

What is more, attempts to increase expression of heterologous protein in a different germplasm with confirmed native high protein levels have not resulted in success. The Illinois High Protein line has been known for some time (see Bhattramakki et al. "Storage Proteins in Illinois High Protein and Illinois Low Protein maize kernels" *Crop Sci.* (1996) 36:1029-1036; Dudley, J. W. and Lambert, R. J. (1992) *Maydica* 37, 81-87). It is a high protein line, with total protein as a percent of dry weight increased in the grain to 30% (as opposed to the usual 8-10%) and as having a 96% increase in zein in the endosperm, mainly α-zeins (19 and 22 kd). It is deficient in globulin 1. However, the inventors have found attempts to use these plants as a host for improved heterologous protein expression result in poor expression of heterologous protein.

This failure to achieve increased expression is instructive for several reasons. First, it demonstrates that whatever the overall protein content of the seed, it is the reduction of alcohol-soluble proteins, such as zeins, that is correlated with increased heterologous protein expression, particularly in the embryo. Further, although one might be motivated to select plants that have higher protein levels, surmising that it will increase heterologous protein levels as well, this is not the case. Thus, whether or not one theorizes a higher or lower protein content in high oil corn, one cannot predict higher expression of heterologous protein. However, the inventors have discovered that high oil corn is an appropriate plant source to increase heterologous expression levels.

When OHS endosperm mutants or high oil germplasm is used as the host to express heterologous protein, the inventors have shown there is an increase in the amount of protein present in the plant tissue. There are considerable commercial advantages to expressing the protein such that it increases in concentration in the tissue. There is less tissue needed for more protein production. Fewer plants need to be grown and processed to achieve a particular amount of protein produced, along with the concomitant advantages of lower transportation costs and less storage area needed. The inventors have surprisingly discovered that such increases can be achieved, not using elite varieties of corn, but using OHS endosperm mutants or high oil varieties. An increase in total soluble protein is not always observed in each instance that heterologous protein is introduced into the germplasm, but the inventors have found that there is a consistent increase in the amount of heterologous protein produced in nanograms per milligram of seed in a pool of plants generated from the germplasm. This is the important measurement for commercial purposes, since in commercial applications, it is the amount of protein that a particular biomass can produce that results in cost savings and increased value. Therefore, when introducing a protein into OHS endosperm mutants or high oil germplasm, within the pool of plants that results, more of those plants will have high heterologous protein expression in the seed. Furthermore, additional increase in expression levels can be achieved when a high oil and OHS endosperm mutant cross is used as the host plant.

In the method of the invention, nucleotide sequences encoding the protein of interest are first introduced into a plant. Such sequences can include any gene which produces a heterologous protein. Examples include, but are not limited to, avidin U.S. Pat. No. 5,767,379), laccase (WO 00/20615), aprotinin (U.S. Pat. No. 5,824,870), β-glucuronidase (U.S. Pat. No. 5,804,694), viral antigens (U.S. Pat. Nos. 6,034,298 and 6,136,320) including TGEV and hepatitis (U.S. Pat. Nos. 5,484,719 and 5,914,123) and proteases (U.S. Pat. No. 6,087,558). The methods available for putting together nucleotide sequences above can differ in detail. However, the methods generally include the designing and synthesis of overlapping, complementary synthetic oligonucleotides which are annealed and ligated together to yield a gene with convenient restriction sites for cloning. The methods involved are standard methods for a molecular biologist.

Once the gene has been isolated which encodes such proteins, it is placed into an expression vector by standard methods. The selection of an appropriate expression vector will depend upon the method of introducing the expression vector into host cells. A typical expression vector contains prokaryotic DNA elements coding for a bacterial replication origin and an antibiotic resistance gene to provide for the growth and selection of the expression vector in the bacterial host; a cloning site for insertion of an exogenous DNA sequence, which in this context would code for the protein of interest; eukaryotic DNA elements that control initiation of transcription of the exogenous gene, such as a promoter; and DNA elements that control the processing of transcripts, such as transcription termination/polyadenylation sequences. it also can contain such sequences as are needed for the eventual integration of the vector into the plant chromosome.

Promoter elements employed to control expression of the protein encoding sequences can be any plant-compatible promoter. Those can be plant gene promoters, such as, for example, the ubiquitin promoter, the promoter for the small subunit of ribulose-1,5-bis-phosphate carboxylase, or promoters from the tumor-inducing plasmids from *Agrobacterium tumefaciens*, such as the nopaline synthase and octopine synthase promoters, or viral promoters such as the cauliflower mosaic virus (CaMV) 19S and 35S promoters or the figwort mosaic virus 35S promoter. See Kay et al., (1987) *Science* 236:1299 and European patent application No. 0 342 926. See international application WO 91/19806 for a review of illustrative plant promoters suitably employed in the present invention. The range of available plant compatible promoters includes tissue specific and inducible promoters.

A tissue specific promoter can be provided to direct transcription of the DNA preferentially to the seed. One such promoter is the globulin promoter. This is the promoter of the maize globulin-1 gene, described by Belanger, F. C. and Kriz, A. L. at (1991) "Molecular Basis for Allelic Polymorphism of the Maize Globulin-1 gene" *Genetics* 129:863-972. It also can be found as accession number L22344 in the Genbank database. Another example is the phaseolin promoter. See, Bustos et al.. (1989) Regulation of β-glucuronidase Expression in Heterologous Tobacco Plants by an A/T-Rich cis-Acting Sequence Found Upstream of a French Bean β-Phaseolin Gene, *The Plant Cell* Vol. 1, 839-853.

In a preferred embodiment, the expression vector also contains a gene encoding a selection marker which is functionally linked to a promoter that controls transcription initiation. For a general description of plant expression vectors and reporter genes, see Gruber et al., "Vectors for Plant Transformation" in *Methods of Plant Molecular Biology and Biotechnology* 89-119 (CRC Press, 1993).

One option for use of a selective gene is a glufosinate-resistance encoding DNA and in an embodiment can be the phosphinothricin acetyl transferase ("PAT"), maize optimized PAT gene or bar gene under the control of the CaMV 35S promoter. The genes confer resistance to bialaphos. See, Gordon-Kamm et al. (1990) *The Plant Cell* 2:603; Uchimiya et al., (1993) *Bio/Technology* 11:835; and Anzai et al., *Mol. Gen. Gen.* 219:492 (1989). A preferred version of the PAT gene is the maize optimized PAT gene, used in the experiments below and which is also described at U.S. Pat. No. 6,096,947.

It may also be desirable to provide for inclusion of sequences to direct expression of the protein to a particular part of the cell. A variety of such sequences are known to those skilled in the art. For example, if it is preferred that expression be directed to the cell wall, this may be accomplished by use of a signal sequence and one such sequence is the barley alpha amylase signal sequence, (BAASS) Rogers, (1985) "Two barley alpha-amylase gene families are regulated differently in aleurone cells" *J. Biol Chem* 260, 3731-3738. Another example is the brazil nut protein signal sequence when used in canola or other dicots. Another alternative is to express the enzyme in the endoplasmic reticulum of the plant cell. This may be accomplished by use of a localization sequence, such as KDEL. This sequence contains the binding site for a receptor in the endoplasmic reticulum. Munro, S. and Pelham, H. R. B. (1987) "A C-terminal signal prevents secretion of luminal ER proteins" *Cell.* 48:899-907.

Obviously, many variations on the promoters, selectable markers and other components of the construct are available to one skilled in the art.

When referring to "introduction" of the nucleotide sequence into a plant, it is meant that this can occur by direct transformation methods, such as *Agrobacterium* transformation of plant tissue, microprojectile bombardment, electroporation, or any one of many methods known to one skilled in the art; or, it can occur by crossing a plant having the heterologous nucleotide sequence with another plant so that progeny have the nucleotide sequence incorporated into their genomes. Such breeding techniques are well known to one skilled in the art.

By way of example, the nucleotide sequence can be introduced by direct transformation into the high oil and/or OHS endosperm mutant plants or can be transformed into another plant, then crossed with the high oil and/or OHS endosperm mutant plants, although the latter is preferred. In yet further enhancement of expression levels, plants having the nucleotide sequence can be crossed with either the high oil or OHS endosperm mutant plants, progeny developed, then that progeny crossed with whichever plant was not used in the first cross, OHS endosperm mutant, or high oil plant, to produce a second set of progeny which includes the genetic background of both plants.

Direct transformation into a plant can occur by one of many techniques known to one skilled in the art and the manner selected is not critical to the practice of the invention. Methods for introducing expression vectors into plant tissue available to one skilled in the art are varied and will depend on the plant selected. Procedures for transforming a wide variety of plant species are well known and described throughout the literature. See, e.g., Miki et al, supra; Klein et al, *Bio/Technology* 10:268 (1992); and Weisinger et al., *Ann. Rev. Genet.*

22: 421-477 (1988). For example, the DNA construct may be introduced into the genomic DNA of the plant cell using techniques such as microprojectile-mediated delivery, Klein et al., *Nature* 327: 70-73 (1987); electroporation, Fromm et al., *Proc. Natl. Acad. Sci.* 82: 5824 (1985); polyethylene glycol (PEG) precipitation, Paszkowski et al., *Embo J.* 3: 2717-2722 (1984); direct gene transfer, WO 85/01856 and EP No. 0 275 069; in vitro protoplast transformation, U.S. Pat. No. 4,684,611; and microinjection of plant cell protoplasts or embryogenic callus. Crossway, *Mol. Gen. Genetics* 202:179-185 (1985). Co-cultivation of plant tissue with *Agrobacterium tumefaciens* is another option, where the DNA constructs are placed into a binary vector system. Ishida et al., "High Efficiency Transformation of Maize (*Zea mays* L.) Mediated by *Agrobacterium tumefaciens*" *Nature Biotechnology* 14:745-750 (1996). The virulence functions of the *Agrobacterium tumefaciens* host will direct the insertion of the construct into the plant cell DNA when the cell is infected by the bacteria. See, for example Horsch et al., *Science* 233: 496-498 (1984), and Fraley et al., *Proc. Natl. Acad. Sci.* 80: 4803 (1983).

Standard methods for transformation of canola are described by Moloney et al. "High Efficiency Transformation of *Brassica napus* Using *Agrobacterium* Vectors" *Plant Cell Reports* 8:238-242 (1989). Corn transformation is described by Fromm et al, *Bio/Technology* 8:833 (1990) and Gordon-Kamm et al, supra. *Agrobacterium* is primarily used in dicots, but certain monocots such as maize can be transformed by *Agrobacterium*. U.S. Pat. No. 5,550,318. Rice transformation is described by Hiei et al., "Efficient Transformation of Rice (*Oryza sativa* L.) Mediated by *Agrobacterium* and Sequence Analysis of the Boundaries of the T-DNA" *The Plant Journal* 6(2): 271-282 (1994), Christou et al, *Trends in Biotechnology* 10:239 (1992) and Lee et al, *Proc. Nat'l Acad. Sci. USA* 88:6389 (1991). Wheat can be transformed by techniques similar to those used for transforming corn or rice. Sorghum transformation is described by Casas et al, supra and by Wan et al, *Plant Physiolog.* 104:37 (1994). Soybean transformation is described in a number of publications, including U.S. Pat. No. 5,015,580.

In one preferred method, the *Agrobacterium* transformation methods of Ishida supra and also described in U.S. Pat. No. 5,591,616, are generally followed, with modifications that the inventors have found improve the number of transformants obtained. The Ishida method uses the A188 variety of maize that produces Type I callus in culture. In one preferred embodiment the Hi-II maize line is used which initiates Type II embryogenic callus in culture. While Ishida recommends selection on phosphinothricin when using the bar or PAT gene for selection, another preferred embodiment provides for use of bialaphos instead.

The bacterial strain used in the Ishida protocol is LBA4404 with the 40 kb super binary plasmid containing three vir loci from the hypervirulent A281 strain. The plasmid has resistance to tetracycline. The cloning vector cointegrates with the super binary plasmid. Since the cloning vector has an *E. coli* specific replication origin, it cannot survive in *Agrobacterium* without cointegrating with the super binary plasmid. Since the LBA4404 strain is not highly virulent, and has limited application without the super binary plasmid, the inventors have found in yet another embodiment that the EHA101 strain is preferred. It is a disarmed helper strain derived from the hypervirulent A281 strain. The cointegrated super binary/cloning vector from the LBA4404 parent is isolated and electroporated into EHA 101, selecting for spectinomycin resistance. The plasmid is isolated to assure that the EHA101 contains the plasmid.

Further, the Ishida protocol as described provides for growing fresh culture of the Agrobacterium on plates, scraping the bacteria from the plates, and resuspending in the co-culture medium as stated in the '616 patent for incubation with the maize embryos. This medium includes 4.3 g MS salts, 0.5 mg nicotinic acid, 0.5 mg pyridoxine hydrochloride, 1.0 ml thiamine hydrochloride, casamino acids, 1.5 mg 2,4-D, 68.5 g sucrose and 36 g glucose, all at a pH of 5.8. In a further preferred method, the bacteria are grown overnight in a 1 ml culture, then a fresh 10 ml culture re-inoculated the next day when transformation is to occur. The bacteria grow into log phase, and are harvested at a density of no more than OD600=0.5 and is preferably between 0.2 and 0.5. The bacteria are then centrifuged to remove the media and resuspended in the co-culture medium. Since Hi-II corn tissue is used, medium preferred for Hi-II is used. This medium is described in considerable detail by Armstrong, C. I. and Green C. E. "Establishment and maintenance of friable, embryogenic maize callus and involvement of L-proline" Planta (1985) 154:207-214. The resuspension medium is the same as that described above. All further Hi-II media are as described in Armstrong et al. The result is redifferentiation of the plant cells and regeneration into a plant. Redifferentiation is sometimes referred to as dedifferentiation, but the former term more accurately describes the process where the cell begins with a form and identity, is placed on a medium in which it loses that identity, and becomes "reprogrammed" to have a new identity. Thus the scutellum cells become embryogenic callus.

It is preferred to select the highest level of expression of the protein, and it is thus useful to ascertain expression levels in transformed plant cells, heterologous plants and tissue specific expression. One such method is an ELISA assay which uses biotinylated anti-enzyme polyclonal antibodies and an alkaline phosphatase conjugate. For example, an ELISA used for quantitative determination of enzyme levels can be an antibody sandwich assay, which utilizes polyclonal rabbit antibodies obtained commercially. The antibody is conjugated to alkaline phosphatases for detection.

The levels of expression of the gene of interest can be enhanced by the stable maintenance of an enzyme encoding gene on a chromosome of the heterologous plant. Use of linked genes, with herbicide resistance in physical proximity to the enzyme encoding gene, would allow for maintaining selective pressure on the heterologous plant population and for those plants where the genes of interest are not lost.

With heterologous plants according to the present invention, enzyme can be produced in commercial quantities. Thus, the selection and propagation techniques described above yield a plurality of heterologous plants which are harvested in a conventional manner. The plant with the enzyme can be used in the processing, or the enzyme extracted. When using the plant itself, it can, for example, be powdered and then applied in the commercial process, or the seed made into flour. Enzyme extraction from biomass can be accomplished by known methods which are discussed, for example, by Heney and Orr, *Anal. Biochem.* 114: 92-96 (1981).

The plant breeding methods used herein are well known to one skilled in the art. For a discussion of plant breeding techniques, see Poehlman (1987) Breeding Field Crops. AVI Publication Co., Westport Conn. Many of the plants which would be most preferred in this method are bred through techniques that take advantage of the plant's method of pollination. A plant is self-pollinating if pollen from one flower is transferred to the same or another flower of the same plant. A plant is cross-pollinated if the pollen comes from a flower on a different plant. For example, in *Brassica*, the plant is normally self sterile and can only be cross-pollinated unless, through discovery of a mutant or through genetic intervention, self compatibility is obtained. In self-pollinating species, such as rice, oats, wheat, barley, peas, beans, soybeans, tobacco and cotton, the male and female plants are anatomically juxtaposed. During natural pollination, the male reproductive organs of a given flower pollinate the female reproductive organs of the same flower. Maize plants (Zea mays L.) can be bred by both self-pollination and cross-pollination techniques. Maize has male flowers, located on the tassel, and female flowers, located on the car, on the same plant. It can self or cross pollinate.

Pollination can be by any means, including but not limited to hand, wind or insect pollination, or mechanical contact between the male fertile and male sterile plant. For production of hybrid seeds on a commercial scale in most plant species pollination by wind or by insects is preferred. Stricter control of the pollination process can be achieved by using a variety of methods of make one plant pool male sterile, and the other the male fertile pollen donor. This can be accomplished by hand detassling, cytoplasmic male sterility, or control of male sterility through a variety of methods well known to the skilled breeder. Examples of more sophisticated male sterility systems include those described at Brar et al., U.S. Pat. Nos. 4,654,465 and 4,727,219 and Albertsen et al. U.S. Pat. Nos. 5,859,341 and 6,013,859.

Backcrossing methods may be used to introduce the gene into the plants. This technique has been used for decades to introduce traits into a plant. An example of a description of this and other plant breeding methodologies that are well known can be found in references such as "Plant Breeding Methodology" edit. Neal Jensen, John Wiley & Sons, Inc. (1988). In a typical backcross protocol, the original variety of interest (recurrent parent) is crossed to a second variety (non-recurrent parent) that carries the single gene of interest to be transferred. The resulting progeny from this cross are then crossed again to the recurrent parent and the process is repeated until a plant is obtained wherein essentially all of the desired morphological and physiological characteristics of the recurrent parent are recovered in the converted plant, in addition to the single transferred gene from the nonrecurrent parent.

When the OHS mutant endosperm trait is controlled by recessive alleles, as with certain opaque plants as indicated above, it will be necessary after crossing the opaque plant with another plant, to cross the resulting progeny with yet another plant from the same opaque plants, and select plants showing the opaque phenotype in order to restore the recessive condition. Alternatively, in a plant such as maize which is capable of self pollination, the pollen can be contacted with silks of the same plant and the progeny screened for the opaque phenotype and restoration to the recessive condition.

When producing a crop of plants as described above, there will be a range of expression levels achieved of heterologous protein. Thus, in a preferred embodiment of the invention, these seeds may be pooled and the plant tissue used directly in the desired end process, or protein extracted from the seed. In another embodiment, it is possible to assay seeds from the plants to select those with the highest expression levels, using this seed for protein source and for further production of plants with maximum expression levels.

The following examples are illustrative of embodiments of the invention but are not intended to limit the scope of same.

EXAMPLE 1

Transformation of Avidin into Plants and Detection of Expression Levels Construction of Plasmids for Avidin Expression in Plants Construction of plasmids for avidin transformation into corn is described in U.S. Pat. No. 5,767,379, incorporated herein by reference. The chicken egg white avidin cDNA was reported by Gope M L, et al., *Nuc. Acids Res.* 15: 3595-3606 (1987). The amino acid sequence was reverse translated into nucleic acid sequence utilizing a preferred maize codon usage table (GCG, assembled by Mike Cherry, Stanford University). From this computer-generated synthetic sequence, overlapping, complementary oligonucleotides with compatible restriction site termini were designed, then annealed and ligated to yield the maize optimized gene. The sequence used is set forth in the '379 patent, incorporated by reference. The barley alpha amylase signal sequence (Rogers J C, supra) was also synthesized (using overlapping, complementary nucleotides) with maize-preferred codons. Compatible restriction sites between these two gene fragments were ligated, with the signal sequence at the 5' end of the avidin gene. The resultant signal sequence/avidin segment was cloned, as a BamHI/EcoRI fragment, into the vector pGEM3Zf+, a product of Promega Corporation (Madison, Wis.), to generate plasmid PHP5142. A BamHI/HpaI fragment containing the signal sequence/avidin region was isolated and cloned into a plasmid (PHP5038) derived from pBlueScript SK+, as a backbone (Stratagene, La Jolla, Calif.). In this plasmid, the signal sequence/avidin gene fragment was inserted between the maize ubiquitin 5' region, which includes the promoter, the first exon and first intron and the potato proteinase inhibitor II (PinII) transcription terminator region. The resultant plasmid is PHP5168 (FIG. 1). Co-transformed with the plasmid is a plasmid containing the bar gene from *Streptomyces hygroscopicus*, supra and White J. (1990) *Nucleic Acids Res* 18:1062 linked to the double 35S promoter (e.g. Friz, S. E. *J Cell Sci* 98:545-550), the intron from the maize alcohol dehydrogenase gene (Callis J., et al. *Genes and Development* 1:1183-1200) and the pinII terminator (An G., et al. (1989) *Plant Cell* 1: 115-122). These constructs and the process used are fully described in the '379 patent, supra. Note that in this experiment the bar gene was used, where in the other experiments described herein the mazie optimized PAT gene was used.

Transformation and Tissue Culture to Produce Avidin-expressing Plants.

An established callus line derived from a single immature embryo of the "Hi-II" maize plants (Armstrong C L, Green C E, Phillips R L (1991) *Maize Gen. Coop. Newsletter*, 65:92-93) was transformed using particle bombardment-mediated transformation with a helium-powered particle acceleration device, PDS 1000 (Bio-Rad, Hercules, Calif.). Hi-II is a corn plant line used in research frequently because of its ease in transformation; it is neither an elite, an OHS endosperm mutant, nor a high oil plant. Tissue showing a friable type-II embryogenic morphology was sieved through 710 m mesh prior to co-transformation with equimolar amounts of the avidin gene (PHP5168) and the bar selectable marker gene (PHP610), according to the procedures of Tomes et al. (Tomes D T, Ross M C, Songstad D D (1995) *Plant Cell Tissue and Organ Culture: Fundamental Methods*. Springer- Verlag, Berlin, Heidelberg. Pp.197-213). Transformants expressing the bar gene were selected in the presence of bialaphos (3 mg l$^{-1}$), according to the protocol of Register et al. (Register J. C.-III et al. (1994), *Plant Mol. Biol.* 25:951-961). Co-transformants that also expressed the avidin gene were identified by ELISA screening of the selected colonies. Multiple plants ($T_0$ generation) were regenerated from avidin-expressing colonies, transferred to the greenhouse and assayed for avidin expression in leaf tissue. $T_1$ seed was obtained by outcrossing, with the $T_0$ plants as the female parent and a non-transformed inbred line (PHN46; see U.S. Pat. No. 5,567,861) as the male parent.

ELISA to Detect Avidin in Corn.

The following procedures were used to detect expression of avidin in seeds. Seeds were powdered and extracted in 10 mM PBS pH 7.0 containing 0.05% Tween-20. Total protein was quantified using the Bradford microtiter assay (Bradford, M. (1976) *Anal. Biochem.* 72:248-254.). ELISAs were typical sandwich style in which the mircrotiter plates were coated with rabbit anti-avidin antibody, the avidin protein was captured overnight at 4° C., and the plate was reacted with goat anti-avidin antibody (Vector Labs, Burlingame, Calif.) followed by anti-goat alkaline phosphatase conjugate (Jackson Immunoresearch, West Grove, Pa.). The alkaline phosphatase was detected with para-nitrophenyl phosphate and read at 405 nm on a SpectroMax plate reader (Molecular Devices, Sunnyvale, Calif.).

EXAMPLE 2

Transformation of Laccase into Plants and Detection of Expression Levels Plant Expression Vectors to Express Laccase The gene for laccase was cloned from *Trametes versicolor* by the methods described here, with isolated RNA reverse transcribed into cDNA. The sequence is set forth at FIG. 2A-C (SEQ ID NOs:1 and 2) and can also be found at Ong., Ed., Brent, W., Pollack, R. and Smith, M. (1997) "Cloning and sequence analysis of two laccases complementary DNAs from the lignolytic *Basidiomycete Trametes versicolor*", *Gene* 196:113-119. See the published application showing expression of laccase in plants, WO 00/206151.

Preparation of Plasmids

Figure 3:
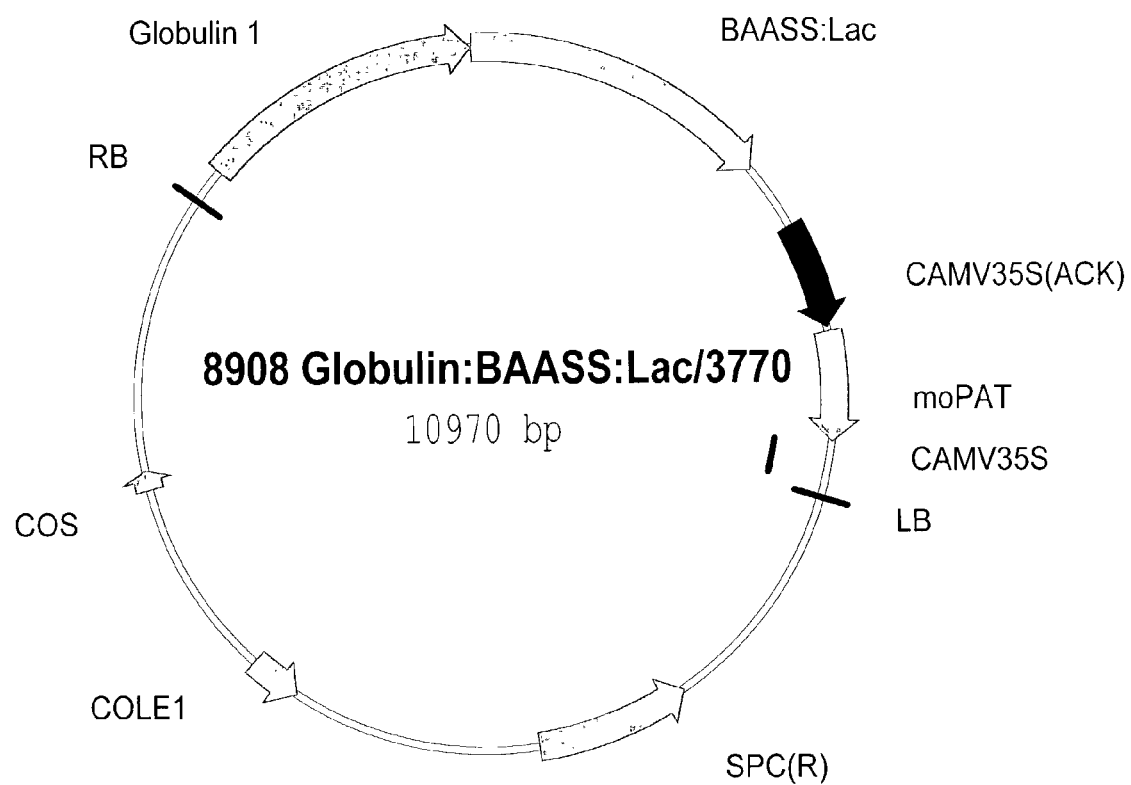
FIG. 3 is the plasmid pPGN 8908 used to introduce sequences encoding the laccase protein into plants.
Figure 4A:
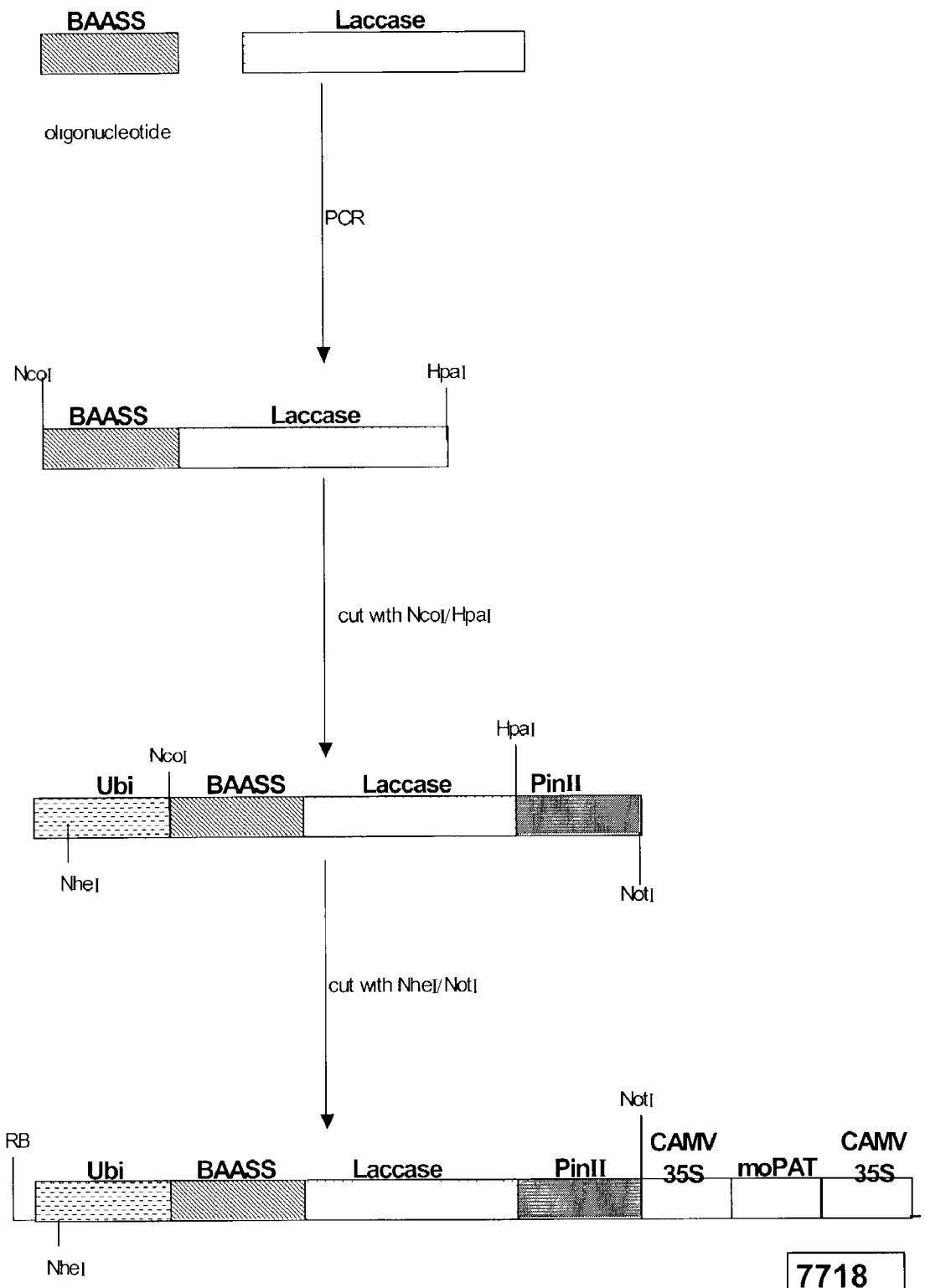
FIG. 4A-B is a diagram of the steps used in preparing pPGN 8908.
Figure 4B:
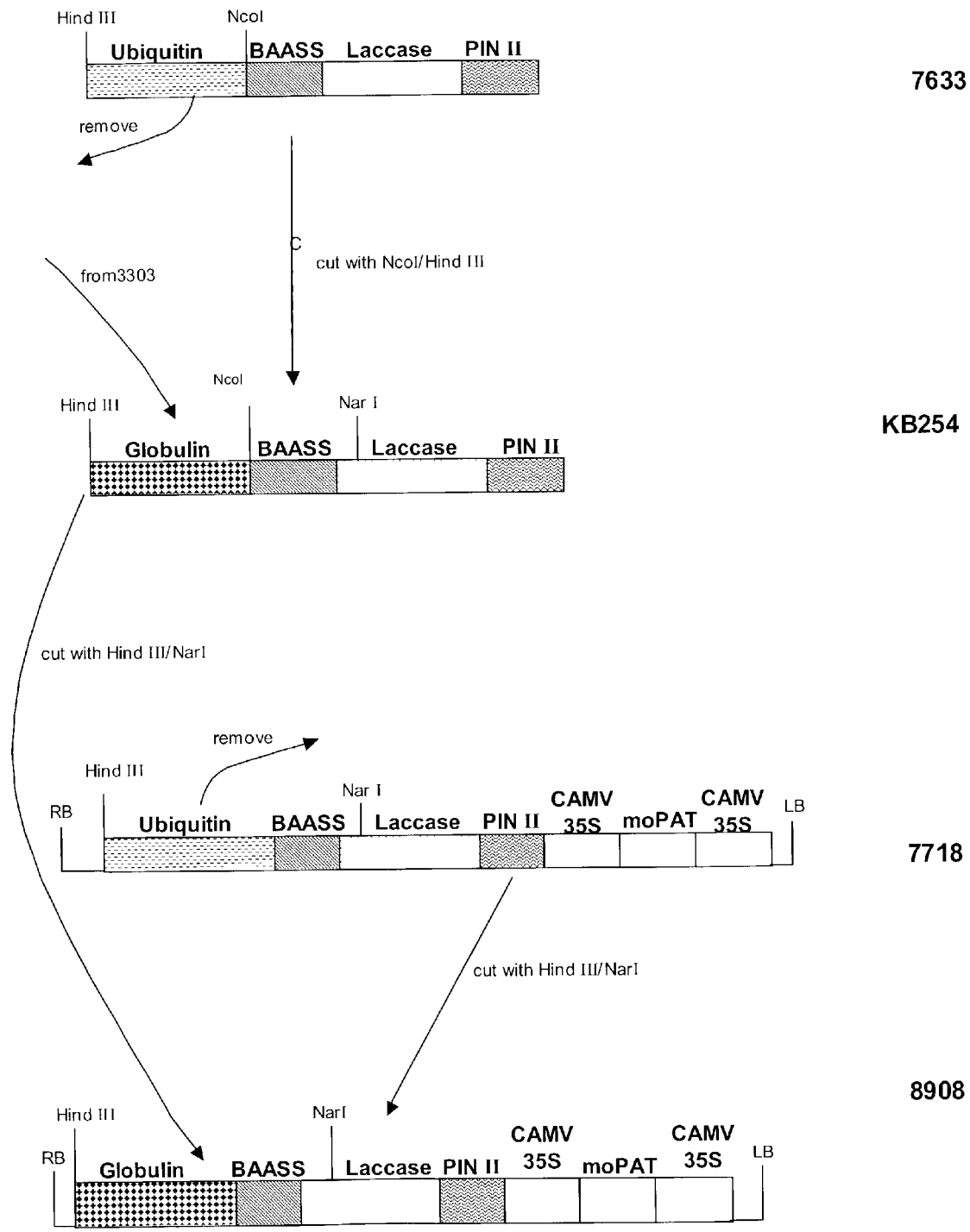

Plasmids containing the barley alpha amylase signal sequences were produced by ligating oligomeric sequences encoding the sequence to the 5' end of the laccase gene, then the entire sequence amplified by PCR and cloned into a vector. The sequencing of individual clones followed and confirmed the presence of the construct. An individual clone was chosen for further manipulations. To generate plasmid pPGN 8908 (FIG. 3) intermediate vectors with BAASS:: laccase were cut with NcoI and HpaI and ligated into vector pPGN 2774, which contains a ubiquitin promoter and PinII terminator. The entire transcription unit was cut from pPGN 2774 with NheI and NotI and ligated to pPGN 3770 containing the 35S promoter with the PAT selectable marker between the left and right borders of the *Agrobacterium tumefaciens*. The ubiquitin promoter of the pPGN 2774 vector removed, substituting the globulin promoter. This is the promoter of the maize globulin-1 gene, described by Belanger, F. C. and Kriz, A. L. at "Molecular Basis for Allelic Polymorphism of the Maize Globulin-1 gene" *Genetics* 129:863-972 (1991). It also can be found as accession number L22344 in the Genebank database. The globulin promoter in pPGN 3303 was cut with HindIII and NcoI, and vector 2774 having the ubiquitin promoter, barley alpha amylase, laccase and PinII sequences was cut with the same restriction enzymes. This process of preparing pPGN 8908 is schematically represented in FIG. 4.

Transformation of Maize

The plant expression units were placed between T-DNA borders in the cloning vector pSB11 from Japan Tobacco Ishida, Yuji, et al. (1996). *Nature Biotechnology* 14, 745-750, Hiei, Yukoh, et al. (1994) *The Plant Journal* 6 (2), 271-282. The vector was mated into *Agrobacterium tumefaciens* strain LBA4404 containing the super binary vector pSB1 (Hiei et al., 1994). After mating, the co- integrated vector, pSB111, was isolated and electroporated into EHA101(Hood, E. E.et al., (1986) *J.Bacteriol.* 168: 1291-1301) and the resulting strain, EHA101(pSB111) used for plant transformation.

Fresh immature zygotic embryos were harvested from Hi-II maize kernels at 1-2 mm in length. The general methods of *Agrobacterium* transformation were used as described by Japan Tobacco, at Ishida as modified and described, supra. Fresh embryos were treated with 0.5 ml log phase *Agrobacterium* strains EHA 101 as described above. Bacteria were grown overnight in a rich medium with kanamycin and spectinomycin to an optical density of 0.5 or greater at 600 nm then re-inoculated in a fresh 10ml culture. The bacteria were allowed to grow into log phase and were harvested at no more dense than OD600=0.5. The bacterial culture was pelleted and resuspended in a co-culture medium.

Individual transformation events were identified when they grew rapidly on the bialaphos-containing medium (3 mg/L). Several plants per transformation event were regenerated from embryogenic calli as described (Hood et al., (1 997) *Molecular Breeding* 3:291-306) and allowed to flower and set seed in the greenhouse. $T_1$ (first generation transformed) seed was planted in back-cross nurseries and crossed to selected inbreds. Grain for processing is produced from these lines.

Extraction of Corn Seed.

Seeds were ground together in a coffee grinder and separate 250 mg aliquots were extracted in 20 mM sodium acetate, pH 5.0 containing 0.05% Tween-20 (SAT) for enzyme assay analysis. Extraction was routinely performed with a 1:2 ratio of seed tissue to buffer. Extracts were centrifuged for 10 minutes at 20,000×g to pellet cell debris and the supernatant was placed in a fresh tube. As is described at WO 01/96543 recovery of active laccase can be increased by adding copper during production or extraction of the laccase. Here the extracts were treated with 10 mM $CuSO_4$ and 0.5M sodium chloride. for one hour at 50° C.

Laccase Microtiter Plate Activity Assay

Protein precipitated by the copper treatments was pelleted by centrifugation for 10 minutes at 20,000×g and the supernatant was transferred to a fresh tube. One to ten µg of soluble corn protein was added per well of a 96-well polystyrene microtiter plate (Costar) containing 140 µl 20 mM sodium acetate pH 5.0 containing 0.05% Tween-20 in each well. The reactions were initiated with 20 µl of 4.5 mM ABTS substrate (Putter, J., and Becker, R., 1981. (1981) in *Methods of Enzymatic Analysis* (Bergemeyer, J. U., ed.) Vo. 3 p. 286, Verlag Chemie, Wienheim) and the microtiter plate was incubated at 25° C. The plates were read at 420 nm on a Spectromax 340 (Molecular Devices) at several times, usually one hour and 18-22 hours total duration depending on the concentration of laccase in the sample. Laccase activity was determined by comparison with known amounts of purified recombinant *Trametes* laccase from *Aspergillis*.

EXAMPLE 3

Crosses to Mutant Plants

The Hi-II transformants were placed into OHS endosperm mutant, Illinois High Protein and/or high oil plants as follows (For ease of reference, in the following paragraph, the OHS endosperm mutant, Illinois high Protein and high oil plants are collectively referred to as "mutant" plants.)

Seed from mutant and transformed plants was planted in ear rows in the field. Leaves of transformed plants were treated with a 1.2% (a.i.) solution of herbicide (Liberty™), and plants showing damage removed. To prevent pollination from nearby wind blown pollen, ears of plants to be used as female parents were covered with a shoot bag before any silks had emerged. Once a sufficient number of silks emerged, the silks were often trimmed to ensure more even pollination. Pollen-shedding tassels from plants to be used as male parents in a cross were covered with a tassel bag secured at the base of the tassel with a paper clip. The next morning the fresh pollen was shaken into the bag and the pollen carried to the female parent. The shoot bag was removed from the ear and the ear immediately covered with the tassel bag containing pollen. The tassel bag was lifted to a vertical position and the pollen shaken over the covered silks. The tassel bag covering the ear was then stapled around the stem of the plant to secure it and the female and male parents in the cross marked on the bag. The ear remained covered until the seed was mature (generally 40-60 days) and then it was harvested, dried and shelled individually. Seed was analyzed in bulk as described above to determine the amount of transgene expression in the seed resulting from the cross.

EXAMPLE 4A

Avidin Expression in High Oil and OHS Endosperm Mutant

The results of introducing avidin into high oil and opaque 2 plants are presented in Table 3. Data were obtained from pools of ten seeds per plant with three different extracts and three different repetitions per extract. The seeds were ground into meal, buffer added, extract obtained, and the solution centrifuged. The supernatant was removed and subjected to three ELISA assays with the mean represented in Table 3 below. This was compared with expression levels obtained in elites that were non-high oil, non-opaque 2 and non-high protein plants.

TABLE 3

| Background | Average % TSP | Range in % TSP | No. of ears |
|---|---|---|---|
| Elite | 7.25 | 1.95-18.36 | 12 |
| ILHP-90 | 5.94 | 2.24-15 | 14 |
| High oil | 10.20 | 0.67-40 | 34 |
| Opaque 2 | 20.38 | 4.72-41.37 | 12 |

As can be seen, both high oil and opaque 2 provided considerable increases in percent soluble protein expression in seed versus the elite varieties. On the other hand, the Illinois High Protein plants showed the worst levels of expression.

EXAMPLE 4B

The above experiment was repeated, this time introducing avidin into an elite or opaque 2 plant or high oil germplasm, and into germplasm that included both opaque 2 and high oil. The same procedures were used, and for crosses that were segregating for the opaque 2 phenotype (i.e. floury, opaque endosperm), 25-seed pools of opaque kernels and vitreous kernels from single ears were analyzed separately for transgene expression. This eliminated all environmental and background genotypic affects and allowed determination of the effect of the opaque 2 gene on transgene expression. The difference between the pool of opaque kernels and the pool of vitreous kernels was that the opaque kernels had two copies of the mutant opaque 2 allele and the vitreous kernels had one copy.

The elite plants used included PHP38 (see U.S. Pat. No. 5,708,189), PHN46 (described at U.S. Pat. No. 5,567,861) and LH244 (described at U.S. Pat. No. 6,252,148). Ohio 43 is an elite germplasm which is a result of a cross of W8 by Ohio 40B as described in Stringfield, G.H. "Maize Inbred Lines of Ohio", Ohio Agriculture Research Station Bulletin, Vo. 831 (1959).

The high oil plants used included PH10A (U.S. Pat. No. 5,861,541) and PH0B3 (See Plant Variety Protection No. 9900041; USDA accession no. PI606344). The opaque plants used were either W23 opaque or vitreous (See USDA accession No. NSL 30060) or W64A vitreous (See USDA accession No. PI587152). In each instance, the elite used was PHP38 (supra). Where a cross was indicated with an opaque, it was crossed with a plant that resulted from a heterologous elite PHN46 containing the avidin gene, itself crossed with an opaque plant.

Figure 5:
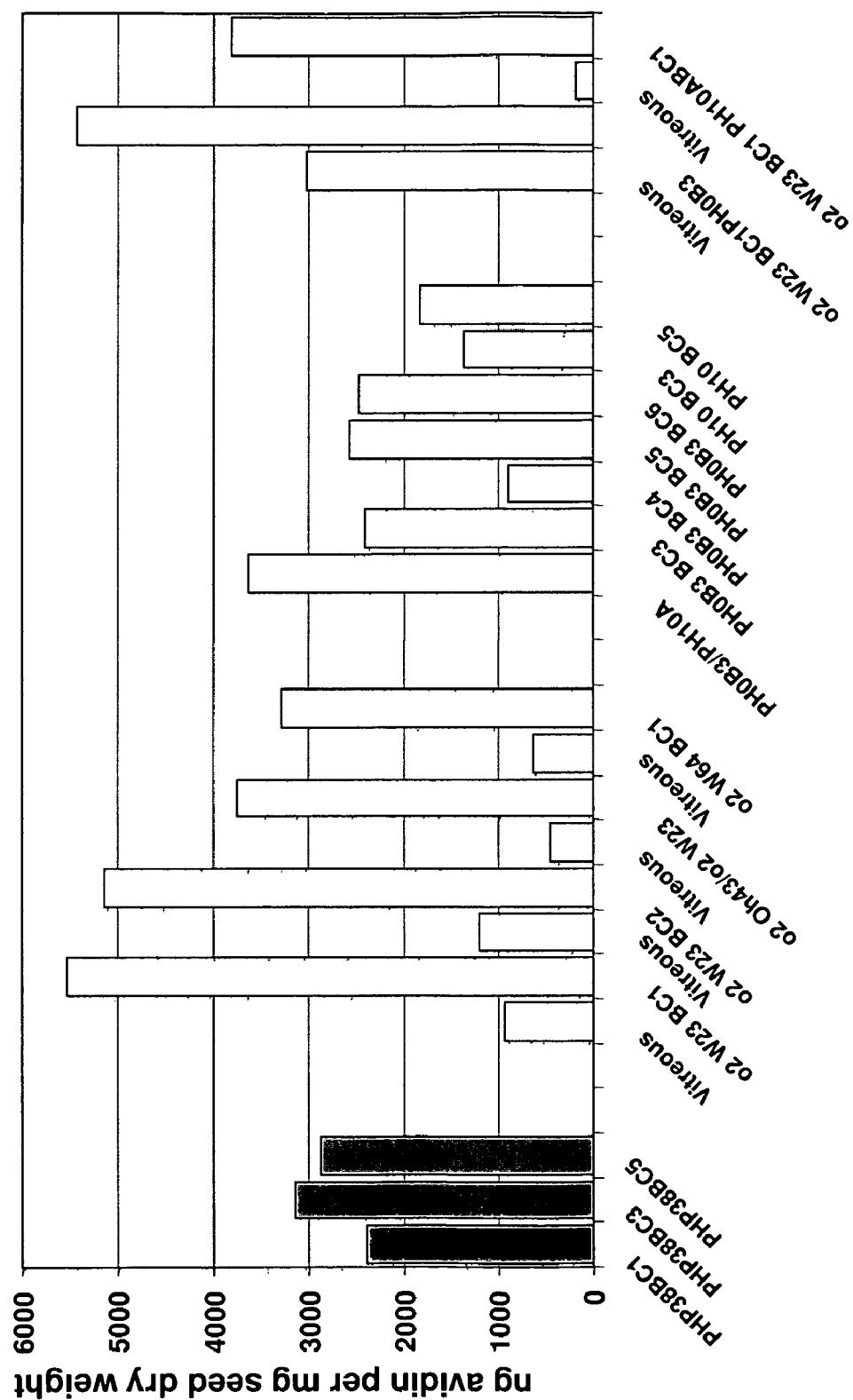
FIG. 5 is a graph which shows the results of avidin expression measured in nanograms of avidin per milligram dry weight of seed, in pooled corn seed, from a single high-expressing ear of corn, where the seed is from elite plants, opaque plants, high oil plants or a combination, as indicated.

Measurements were taken of expression levels from seed of an ear of each one of the plants, with a high-expressing ear selected from each germplasm source. Seed was pooled from that ear and measured. FIG. 5 is a graph showing the results. The first three bars grouped together show use of elite germplasm alone. The next group of eight bars shows use of opaque or vitreous germplasm. The third group of seven bars shows results when crossing into high oil germplasm. The final group of four bars shows crossing into both opaque 2 and high oil, compared to vitreous germplasm. "BC" refers to the number of backcrosses.

The elite germplasm host showed good expression of avidin, and was measured from a plant with one backcross into the germplasm, and two other ears with a third and fifth backcross. The expression levels in the vitreous plant host were quite low, and, as can be seen, expression in the opaque 2 host plant was markedly higher that either elite or vitreous plant host expression levels. Further backcrossing into the germplasm did not improve expression levels further, nor did crossing with both elite and opaque 2 germplasm.

As the results show, using elite plants provides satisfactory expression levels of the heterologous avidin protein. When opaque or high oil plants are used, improvement in expression is obtained. Improvement is obtained when the high oil plant is crossed to opaque plants. Note that when the plant is opaque, that is not vitreous, and has reduced levels of alcohol soluble protein in the endosperm, up to 15 times increased expression level is obtained. When the plant seed is vitreous, that is not reduced in alcohol soluble protein levels in the endosperm, quite poor expression is obtained. This further reflects that the plant provides poor expression when it is vitreous, but when the endosperm has reduced alcohol soluble levels, enhancement is obtained.

EXAMPLE 5

Laccase Expression in High Oil Plants

Seedlings of the Hi-II laccase transformants were transplanted into soil in the greenhouse and allowed to flower and produce seed through hand-pollinations with pollen from high oil plants.

Figure 6:
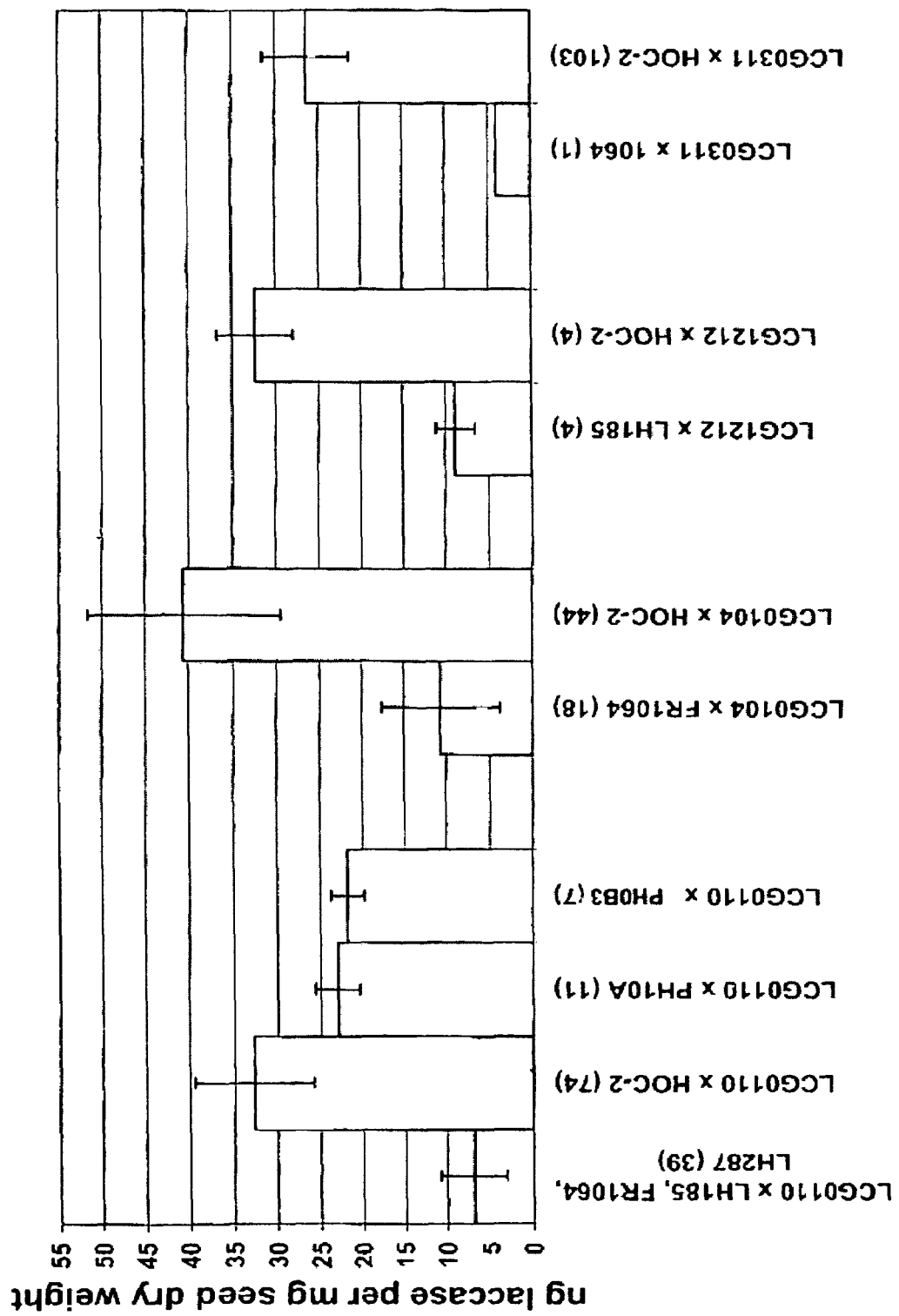
FIG. 6 is a graph showing expression of laccase measured in nanograms of laccase per milligram dry weight of seed, where expressed in elite or high oil plants.

Results are reflected in FIG. 6. The graph shows expression of laccase in high oil corn, where seed was taken from ears collected from the germplasm. The number of ears taken from each germplasm is shown in parentheses.

The laccase gene was initially transformed into Hi-II and crossed into the Illinois High Protein germplasm. The result of this cross was poor expression. Following this, it was backcrossed into high oil germplasm a sufficient number of times so that the ILHP germplasm was nearly extinguished from the resulting plant. HOC2 refers to a high oil line produced from the Illinois High Oil Alexho lines described supra. The other high oil line used was PH0B3, supra. The reference LH 185 refers to an elite line, described in U.S. Pat. No. 5,491,294. FR1064 is another elite line which is a derivative of FR1141, as described in Anon. (1989) "Seedsmans' Handbook" 16$^{th}$ Edit. Mike Brayton Seeds, Inc., Ames, Iowa. As can be seen, when high oil plants are used as the protein host, increased levels of heterologous expression result.

EXAMPLE 6

Expression of Brazzein Protein in OHS Endosperm Mutant and High Oil Plants

Figure 7:
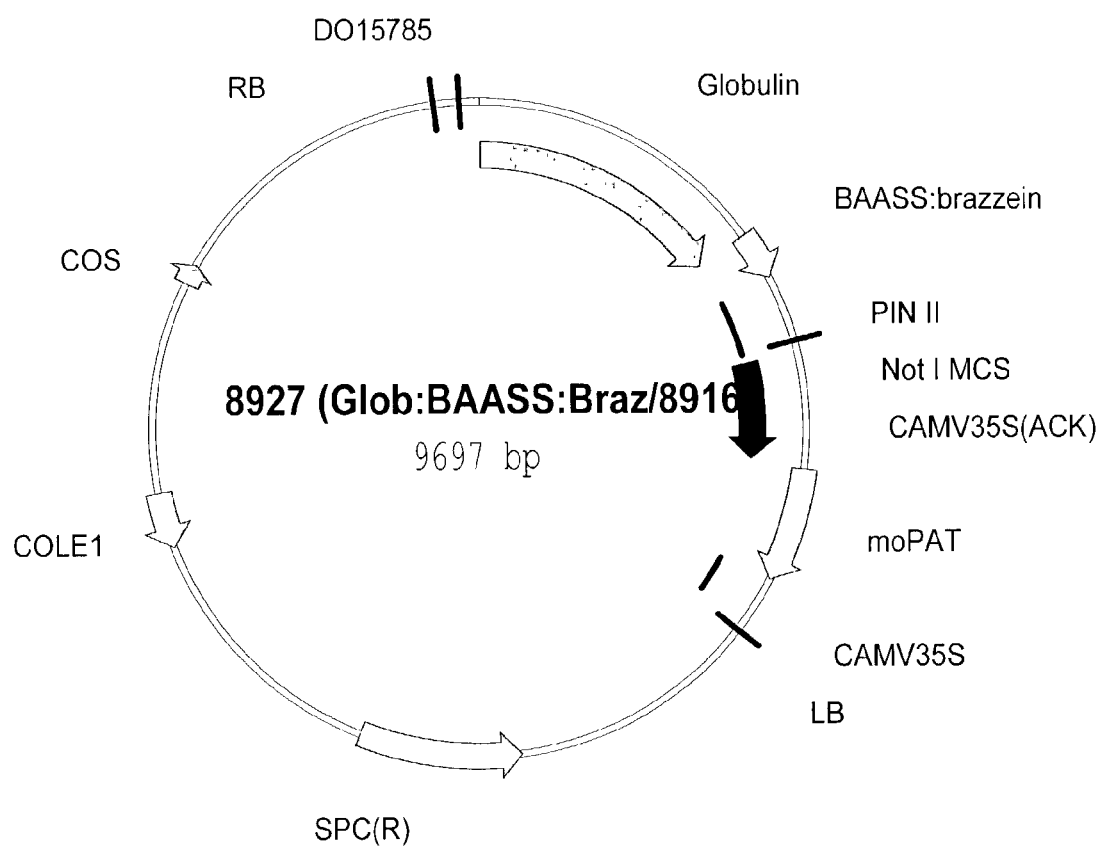
FIG. 7 shows plasmid pPGN 8927 used to introduce sequences encoding the brazzein protein into plants.

The experiment was again repeated, this time introducing the protein brazzein into opaque or high oil plants using the process described supra. Brazzein is a protein which can be used commercially as a sweetener. Nucleotide sequences have been identified which encode the brazzein protein, and an example is that disclosed at U.S. Pat. No. 5,346,998, incorporated herein by reference. (See also U.S. Pat. No. 5,741,537 showing use of the DNA and protein in food). In this particular experiment, the sequence was a slightly modified version found at Genbank accession number P56552 and is as set forth (SEQ ID NO:3):

caggacaagtgcaagaaggtgtacgagaactacccggtgtccaagtgccag ctcgccaaccagtgcaactacgactgcaagctcgacaagcacgcccgctcc ggcgagtgcttctacgacgagaagcgcaacctccagtgcatctgcgactac tgcgagtac As in the methods described above, the sequence was placed into plasmid pPGN8927, shown in FIG. 7. The first step in constructing PGN8927 was to design a codon optimized DNA sequence encoding brazzein for expression in corn. Oligonucleotides were then obtained from an outside synthesis laboratory. These oligonucleotides overlapped one another and together covered the brazzein coding sequence. They were annealed to give the full-length sequence and this sequence was then amplified by PCR using shorter oligonucleotides that would anneal to each end of the synthetic brazzein gene. A further oligonucleotide spanning the barley alpha amylase signal sequence (BAASS) and overlapping with the brazzein gene was then annealed to the coding sequence. A further PCR procedure was then completed using one oligonucleotide located at the 5' end of DNA encoding BAASS and one oligonucleotide located at the 3' end of DNA encoding brazzein. The resulting molecule was a BAASS-brazzein fusion sequence. The oligonucleotides were designed to include an NcoI restriction endonuclease site at the 5' end of BAASS and an HpaI restriction endonuclease site at the 3' end of brazzein. This PCR product was cloned into a TA based vector of Stratagene. The second step was to sub-clone an NcoI-HpaI restriction enzyme fragment from the TA vector/brazzein plasmid into the vector PGN2774, so placing the potato PinII terminator sequence downstream of the brazzein coding sequence. In the third step, a HindIII-NcoI fragment spanning the maize globulin1 promoter was introduced into this new BAASS-Brazzein-PinII plasmid to place the globulin 1 promoter upstream of the brazzein coding sequence. In the final step a HindIII-NotI fragment spanning the entire Globulin1:BAASS:Brazzein:PinII transcription unit was introduced into the plant transformation vector PGN8916. This vector was introduced by *Agrobacterium* transformation processes described supra into Hi-II plants.

Figure 8:
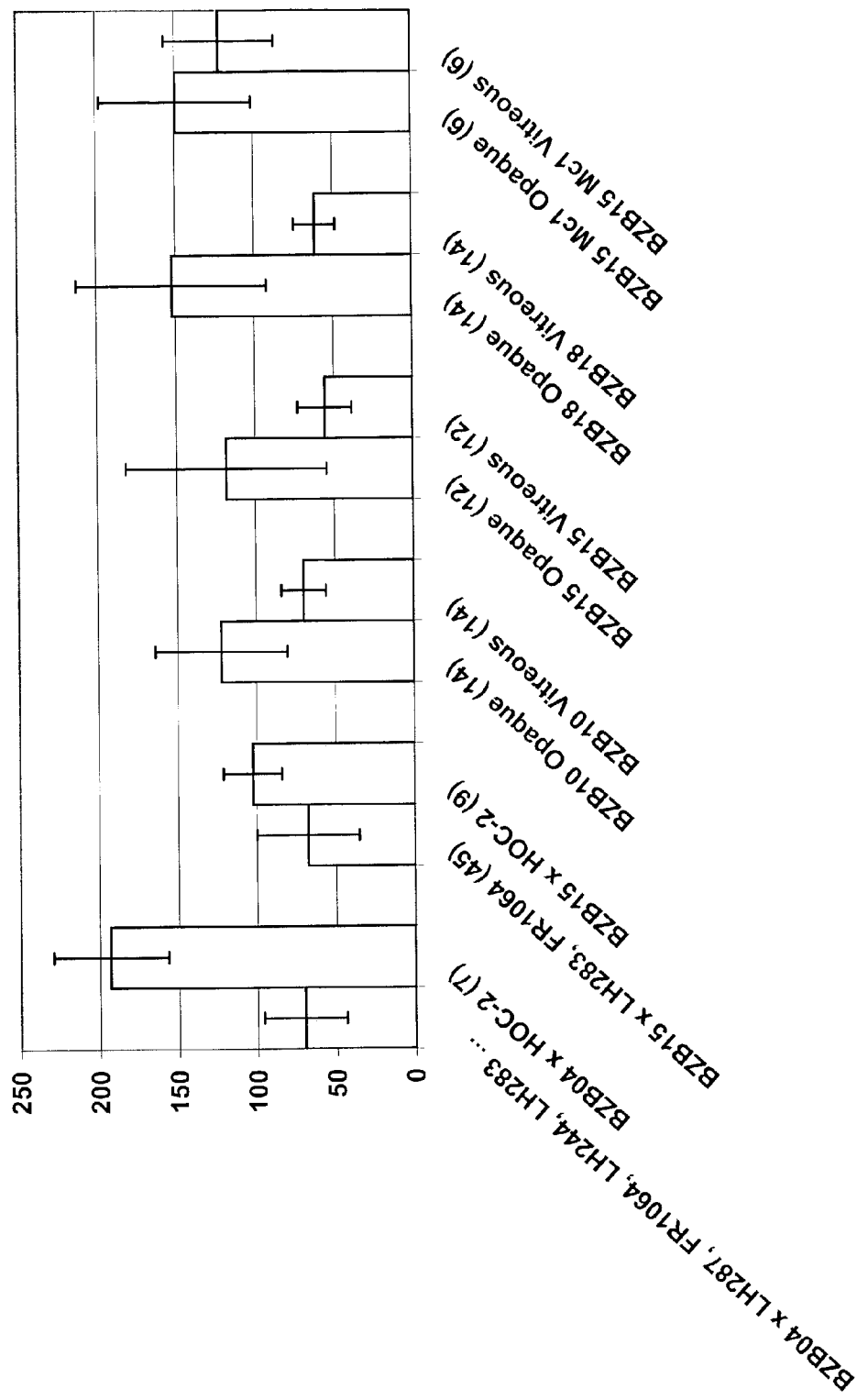
FIG. 8 is a graph showing expression of brazzein protein measured in nanograms of brazzein per milligram dry weight of seeds, where expressed in either elite, high oil, vitreous, opaque or mucronate corn plants, as indicated. The number of ears in the particular sample is listed in parentheses next to the designation.

The Hi-II plant was crossed into elite, mucronate, opaque 2, vitreous or high oil HOC, supra) plants. Ears of corn were collected (the number in parentheses) and expression of seed on the ears pooled. The results are set forth in FIG. 8. The OHS endosperm mutant germplasm, whether it was opaque 2 or mucronate, provided higher expression levels than with elite, and considerably higher than in vitreous germplasm. High oil germplasm lines provided higher expression levels as well.

EXAMPLE 7

Expression of Aprotinin Protein in High Oil Plants

Figure 9:
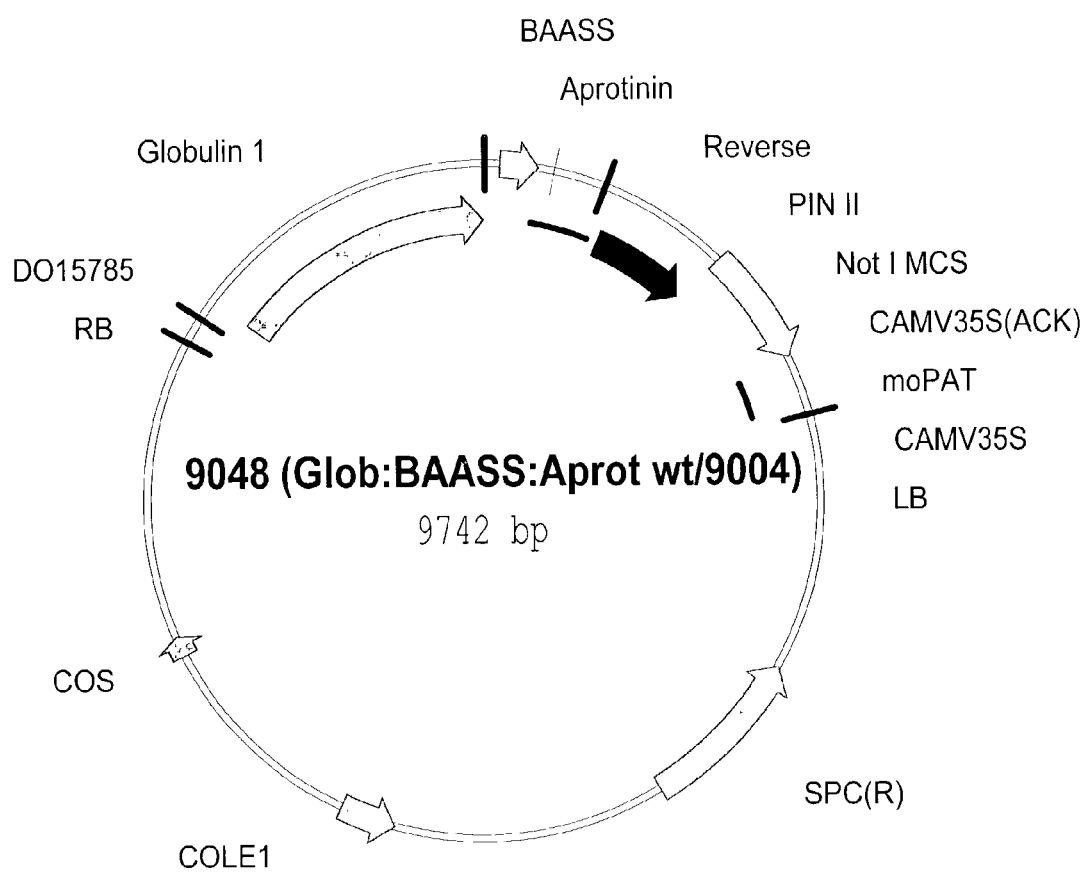
FIG. 9 shows plasmid pPGN 9048 used to introduce sequences encoding aprotinin into plants.

The experiment was repeated, this time expressing the protein aprotinin, a protein used in a variety of pharmaceutical and hospital settings. The aprotinin gene and its expression in plants are described at U.S. Pat. No. 5,824,870, incorporated herein by reference. There were several changes in the method used in this experiment from that set forth in the patent. The method of corn transformation used was not bombardment, but *Agrobacterium* transformation, described supra. Two amino acid changes were made in the sequence, and it is set forth below (SEQ ID NO:4):

cgcccggacttctgcctcgagccgccatacaccggaccctgcaaggccagg atcatccgctacttctacaacgccaaggccggcctctgccagaccttcgtt tacggaggctgccgcgccaagcgcaacaacttcaagagcgctgaggactgc atgcgcacctgcggaggcgcc The sequence encoding aprotinin was placed into vector pPGN9048, shown in FIG. 9. The first step in constructing PGN9048 was to design a codon optimized DNA sequence encoding aprotinin for expression in corn. Oligonucleotides were then obtained from an outside synthesis laboratory. These oligonucleotides overlapped one another and together covered the aprotinin coding sequence. They were annealed to give the full-length sequence and this sequence was then amplified by PCR using shorter oligonucleotides that would anneal to each end of the synthetic aprotinin gene. A further oligonucleotide spanning the barley alpha amylase signal sequence (BAASS) and overlapping with the aprotinin gene was then annealed to the coding sequence. A further PCR procedure was then completed using one oligonucleotide located at the 5' end of DNA encoding BAASS and one oligonucleotide located at the 3' end of DNA encoding aprotinin. The resulting molecule was a BAASS-aprotinin fusion sequence. The oligonucleotides were designed to include an NcoI restriction endonuclease site at the 5' end of BAASS and an HpaI restriction endonuclease site at the 3' end of aprotinin. This PCR product was cloned into a TA based vector of Stratagene. The second step was to sub-clone an NcoI-HpaI restriction enzyme fragment from the TA vector/aprotinin plasmid into the vector PGN2774, so placing the potato PinII terminator sequence downstream of the aprotinin coding sequence. In the third step, a HindIII-NcoI fragment spanning the maize globulin 1 promoter was introduced into this new BAASS-Aprotinin-PinII plasmid to place the globulin 1 promoter upstream of the aprotinin coding sequence. In the final step a HindIII-NotI fragment spanning the entire Globulin1: BAASS:Aprotinin:PinII. The aprotinin-encoding sequence was introduced into elite germplasm LH244 supra, and into high oil germplasm (HOC-2, supra) used as the female parent.

Figure 10:
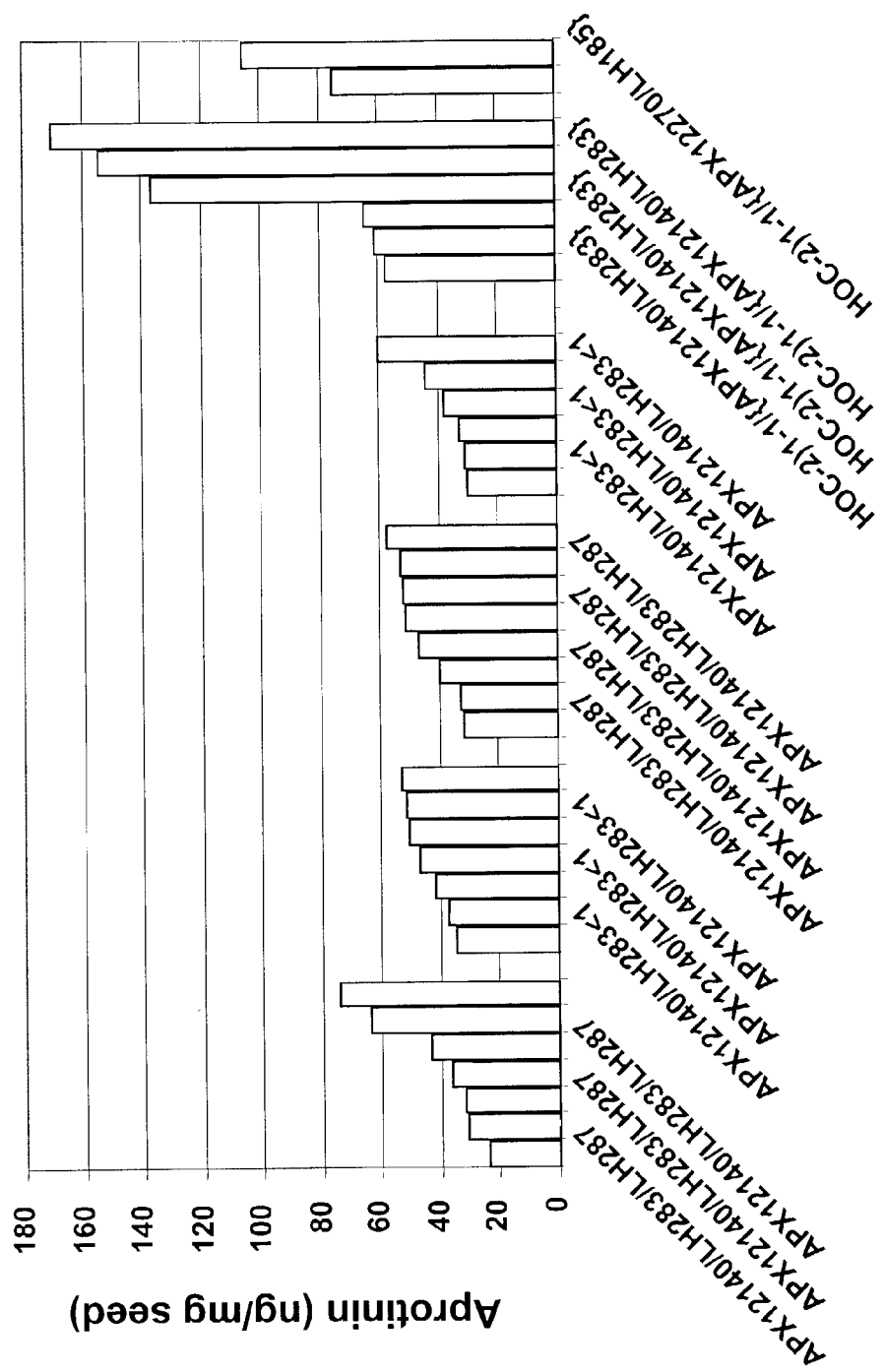
FIG. 10 is a graph showing expression of aprotinin protein measured in nanograms of aprotinin per milligram of dry weight of seeds, where expressed in elite plants (see the shaded bars) or high oil plants (not shaded). The numbers represent measurements from individual ears of corn.

The results are shown in the graph of FIG. 10. Again, it can be seen that use of elite germplasm provides satisfactory levels of expression, and that using high oil germplasm provided more plants with higher expression levels of the protein.

EXAMPLE 8

Expression of Trypsin in OHS Endosperm Mutant and High Oil Plants

In this experiment, the protein trypsinogen was introduced into high oil and opaque germplasm using the *Agrobacterium* transformation process and breeding processes described supra. Trypsin is produced from trypsinogen and is a protease used in the biological sciences and medical fields. The trypsinogen gene used here was made publicly available through Genbank, as accession number P00760. The sequence and method of introducing trypsinogen into plants is described at U.S. Pat. No. 6,087,558, incorporated herein by reference.

Figure 11:
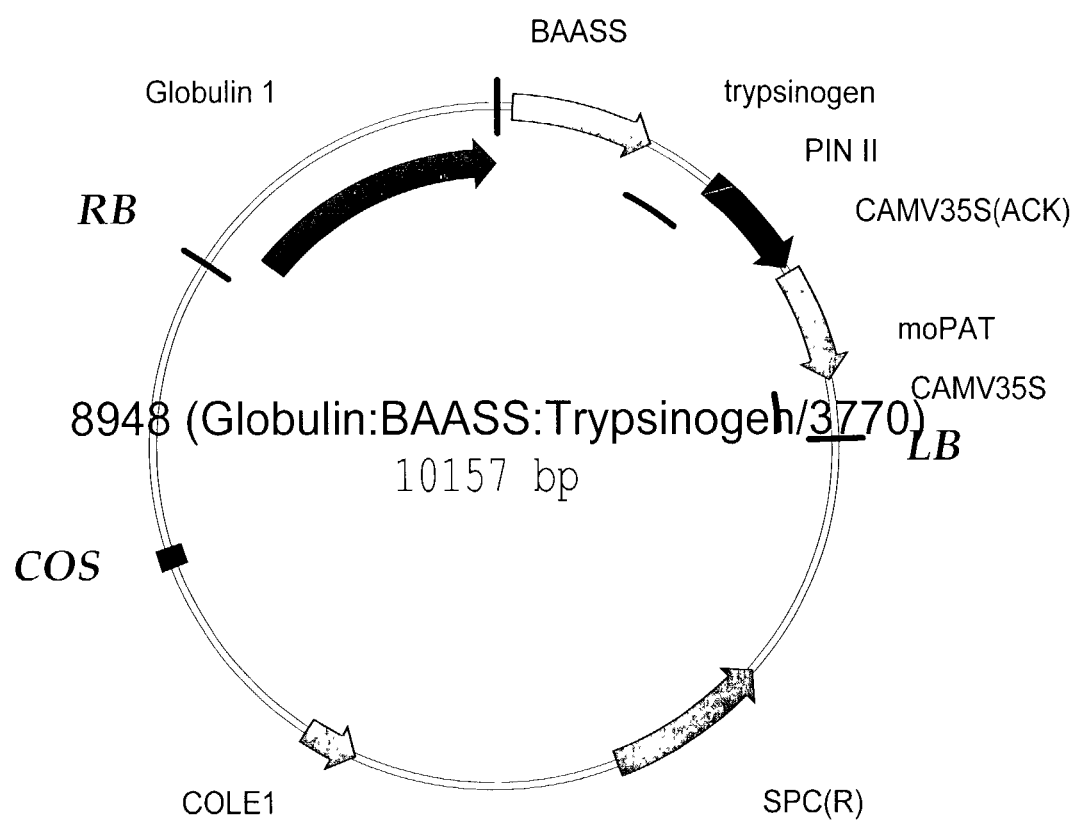
FIG. 11 shows plasmid pPGN 8948 used to introduce sequences encoding the trypsinogen protein into plants.

In this instance the sequence was placed in plasmid pPGN8948 shown in FIG. 11. The first step in constructing PGN8948 started with a cDNA sequence encoding trypsinogen with the Genbank accession number D38507. An oligonucleotide spanning the barley alpha amylase signal sequence (BAASS) and overlapping with the trypsinogen gene was then annealed to the coding sequence. A PCR procedure was then completed using one oligonucleotide located at the 5' end of DNA encoding BAASS and one oligonucleotide located at the 3' end of DNA encoding trypsinogen. The resulting molecule was a BAASS-trypsinogen fusion sequence. The oligonucleotides were designed to include an NcoI restriction endonuclease site at the 5' end of BAASS and an HpaI restriction endonuclease site at the 3' end of trypsinogen. This PCR product was cloned into a TA based vector of Stratagene. The second step was to sub-clone an NcoI-HpaI restriction enzyme fragment from the TA vector/trypsinogen plasmid into the vector PGN2774, so placing the potato PinII terminator sequence downstream of the trypsinogen coding sequence. In the third step, a HindIII-NcoI fragment spanning the maize globulin1 promoter was introduced into this new BAASS-Trypsinogen-PinII plasmid to place the globulin 1 promoter upstream of the trypsinogen coding sequence. In the final step a HindIII-NotI fragment spanning the entire Globulin1:BAASS:Trypsinogen:PinII transcription unit was introduced into the plant transformation vector PGN3770. It was introduced, using methods described above, into elite (LH244, supra or LH283, see U.S. Pat. No. 5,773,683), high oil (HOC, supra)and opaque (W23, supra) germplasm.

Figure 12:
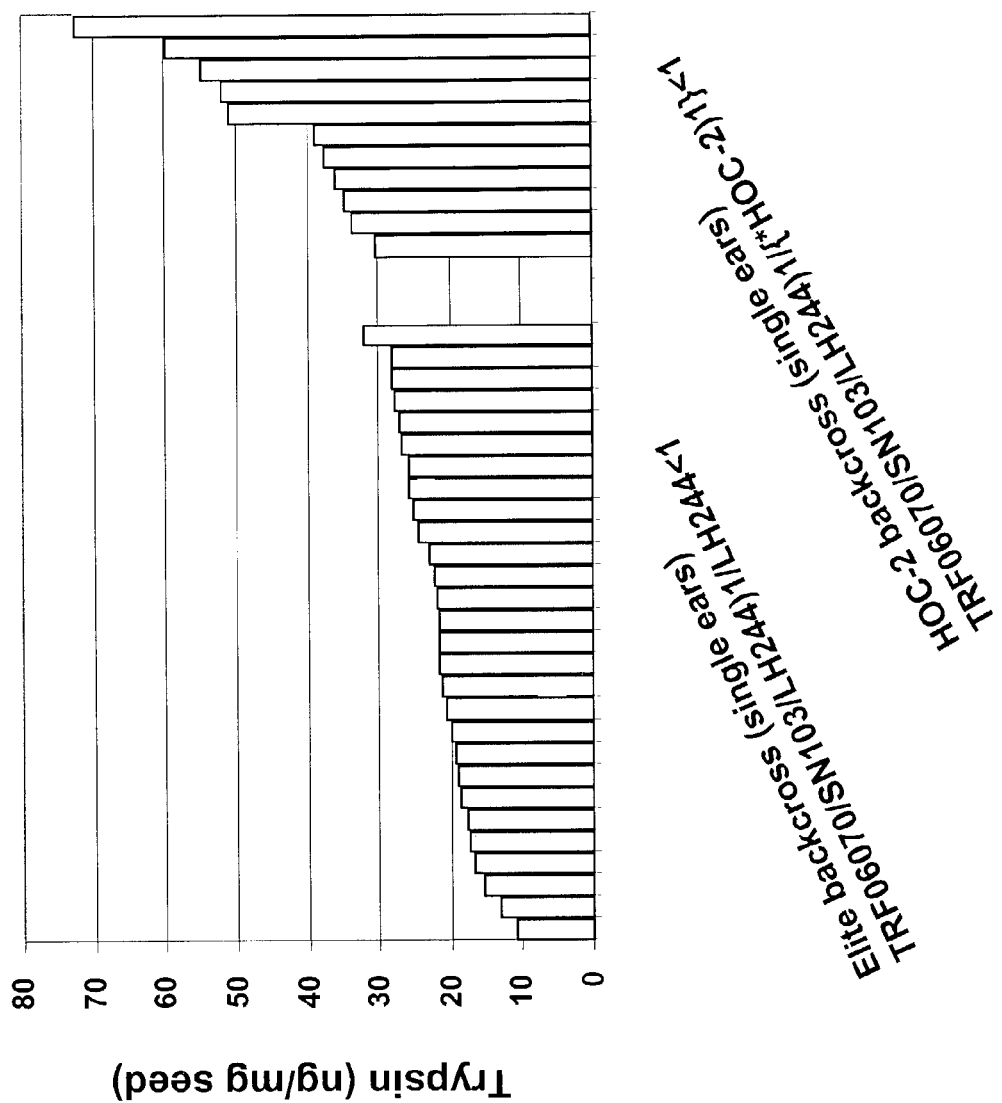
FIG. 12 is a graph showing expression of trypsin protein measured in nanograms of trypsin per milligram of dry weight of seed, where expressed in elite or high oil plants, as indicated. The data are collected from seed from single ears of corn.
Figure 13:
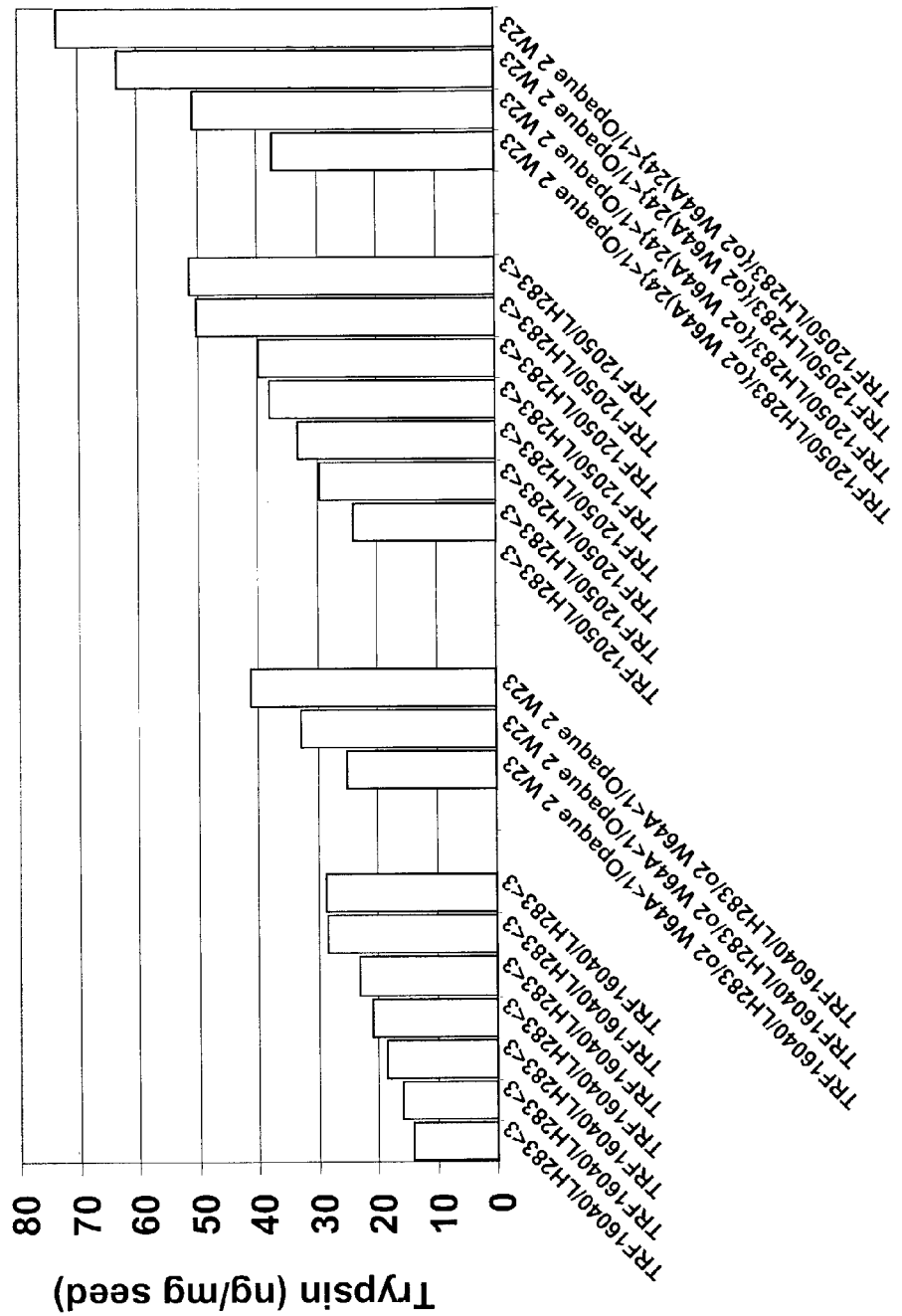
FIG. 13 is a graph showing expression of trypsin protein measured in nanograms of trypsin per milligram of dry weight of seed, where expressed in elite or opaque plants, as indicated, with seed taken from individual ears.

FIG. 12 shows results of measuring seed from individual ears of corn with each bar on the graph representing measurement of pooled seed from one ear. Each bar represents an ear of corn. High oil germplasm provided more seed with higher expression levels of the trypsinogen. In FIG. 13, a comparison of results with the elite germplasm LH283 and opaque 2 corn is shown in measurements of seed taken from a single ear, using two different events. The first event is labeled TRF16040, and was crossed into either the elite germplasm or opaque 2 germplasm. Opaque 2 germplasm, it can be seen provided higher expression levels from this event. The second event is labeled TRF 12050. Again, opaque 2 germplasm provided higher expression levels.

EXAMPLE 9

Expression of Managenese Peroxidase in High Oil Plants

Figure 15:
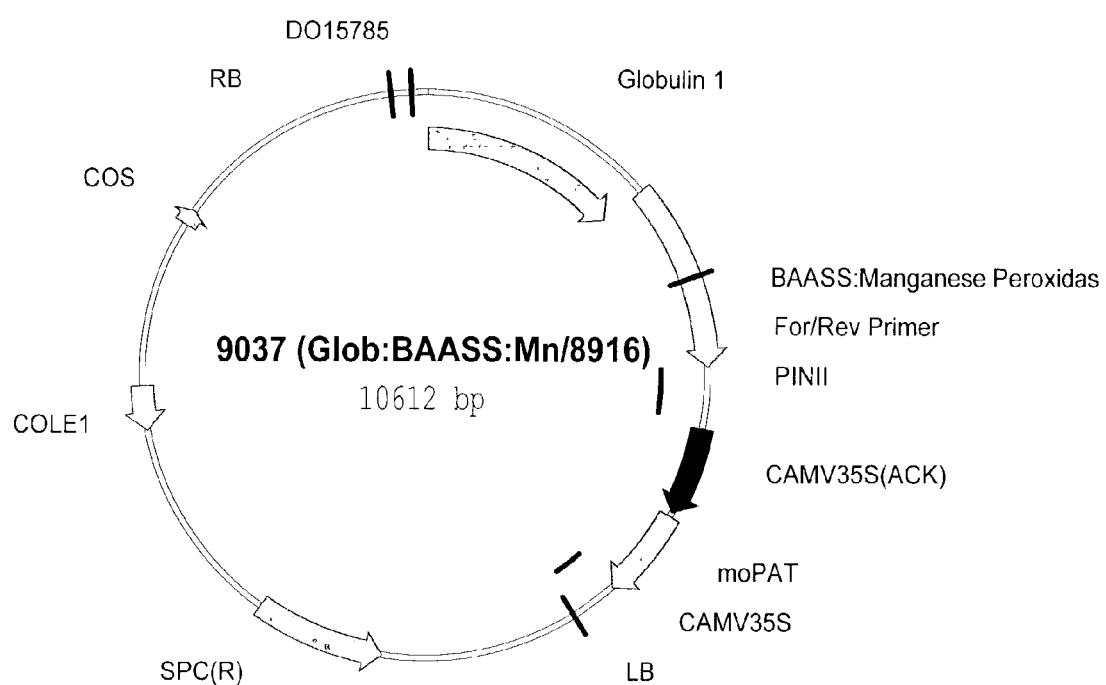
FIG. 15 shows plasmid pPGN 9037 used to introduce manganese peroxidase into plants.

In this experiment, the protocols were repeated, this time-transforming Hi-II by *Agrobacterium* transformation and introducing the manganese peroxidase-encoding gene into high oil germplasm using processes described supra.. The protein is used for its degradation properties in the pulp and paper industry. The gene used in the present invention is from *Phanerochaete chrysosporium* and is set forth in FIG. 14A and B (SEQ ID NOs:5 and 6). The sequence was placed into plasmid pPGN9037, set forth in FIG. 15.

A vector containing a cDNA for manganese peroxidase and a fungal secretion signal has been described before; see Stewart et al. 1996. Efficient expression of a *Phanerochaete chrysosporium* manganese peroxidase gene in *Aspergillus oryzae*. Appl. Environ. Microbiol. 62:860-864. The secretion signal was removed to replace the fungal signal sequence with the barley alpha amylase signal sequence (BAASS). The BAASS, which contains an NcoI site and the initiating methionine codon, was added to the 5' end of the cDNA using PCR resulting in a BAASS:: : manganese peroxidase construct. An HpaI restriction site was added to the 3' end of the cDNA using PCR. The resulting NcoI-HpaI fragments, were ligated into the BbsI-HpaI vector fragment from p2774 which contains the ubiquitin promoter and the Pin II terminator sequences resulting in plasmid K2704. The HindIII-NcoI ubiquitin promoter fragment from K2704 was removed and replaced with the HindIII-NcoI fragment from pPGN7583 which contains the PGNpr6 promoter (WO 01/94394) resulting in K2792 and K2781 respectively. This modified ubiquitin-like promoter lacks a 5' heat shock sequence and is set forth below (SEQ ID NO:7):

```
gtgcagcgtgacccggtcgtgcccctctctagagataatgagcattgcatgtctaagttataaaaaattaccacatatttttttgtc acacttgtttgaagtgcagtttatctatctttatacatatatttaaactttactctacgaataatataatctatagtactacaataatatca gtgttttagagaatcatataaatgaacagttagacatggtctaaaggacaattgagtattttgacaacaggactctacagttttatct
```

-continued

```
ttttagtgtgcatgtgttctcctttttttttgcaaatagcttcacctatataatacttcatccattttattagtacatccatttagggtttagg gttaatggtttttatagactaattttttttagtacatctattttattctattttagcctctaaattaagaaaactaaaactctattttagttttttt atttaataatttagatataaaatagaataaaataaagtgactaaaaattaaacaaatacccttaagaaattaaaaaaactaaggaa acattttcttgtttcgagtagataatgccagcctgttaaacgccgtcgacgagtctaacggacaccaaccagcgaaccagcag cgtcgcgtcgggccaagcgaagcagacggcacggcatctctgtcgctgcctctcgagagttccgctccaccgttggacttgc tccgctgtcggcatccagaaattgcgtggcggagcggcagacgtgagccggcacggcaggcggcctcctcctcctctcac ggcacggcagctacgggggattcctttcccaccgctccttcgctttccttcctcgcccgccgtaataaatagacacccctcc acaccctctttccccaacctcgtgttgttcggagcgcacacacacacaaccagatctccccaaatccaccgtcggcacctc cgcttcaaggtacgccgctcgtcctccccccccccccctctctaccttctctagatcggcgttccggtccatggttagggcccg gtagttctacttctgttcatgtttgtgttagatccgtgtttgtgttagatccgtgctgctagcgttcgtacacggatgcgacctgtacg tcagacacgttctgattgctaacttgccagtgtttctctttggggaatcctgggatggctctagccgttccgcagacgggatcgat ttcatgattttttttgtttcgttgcatagggtttggtttgccctttcctttatttcaatatatgccgtgcacttgtttgtcgggtcatcttttc atgctttttttttgtcttggttgtgatgatgtggtctggttgggcggtcgttctagatcggagtagaattctgtttcaaactacctggtg gatttattaattttggatctgtatgtgtgtgccatacatattcatagttacgaattgaagatgatggatggaaatatcgatctaggata ggtatacatgttgatgcgggttttactgatgcatatacagagatgcttttgttcgcttggttgtgatgatggtgtggttgggcgg tcgttcattcgttctagatcggagtagaatactgtttcaaactacctggtgtatttattaattttggaactgtatgtgtgtgtcatacat cttcatagttacgagtttaagatggatggaaatatcgatctaggataggtatacatgttgatgtgggttttactgatgcatatacatg atggcatatgcagcatctattcatatgctctaaccttgagtacctatctattataataaacaagtatgttttataattattttgatcttgat atacttggatgatggcatatgcagcagctatatgtggattttttagccctgccttcatacgctatttatttgcttggtactgtttcttt gtcgatgctcaccctgttgtttggtgttacttctgca
```

The HindIII-NotI fragment from K2781 was then ligated into the HindIII-Not I vector fragment from PGN8916, which contains the 35S:PAT, PGN8998 (BAASS:manganese peroxidase) respectively. To generate plasmid pPGN9037, the NcoI-NotI fragment from K2781 containing BAASS:manganese peroxidase along with the HindIII-NcoI fragment from KB381 containing the Globulin 1 promoter were ligated into the HindIII-NotI vector fragment from PGN8916 resulting in the final Globulin:BAASS:manganese peroxidase vector PGN9037. Seeds of transgenic maize plants were analyzed by a MnP activity assay. Transgenic maize seed samples were homogenized individually with a custom seed pulverizer or in bulks of 50 seeds in a coffee grinder and extracted in 50 mM sodium tartrate pH 4.5. Protein concentration of the extracts was determined by the method of Bradford, with BSA as standard (Bradford, M. 1976. Anal. Biochem. 72:248).

MnP activity in the extracts was measured by monitoring the oxidation of 2,6-dimethoxyphenol at 469 nm (Wariishi et al. 1992. Manganese(II) oxidation by manganese peroxidase from the basidiomycete *Phanerochaete chrysosporium*. Kinetic mechanism and role of chelators. J. Biol. Chem. 267: 23688-23695). Briefly, 0.2-10 microgram of seed extract was assayed at 28° C. for 5 minutes in 50 mM tartrate pH 4.5 containing 0.5 mM manganese sulfate, 1 mM 2,6-dimethoxphenol, and 0.05 mM hydrogen peroxide.

The results are shown in the graph of FIG. 16. The shaded bars on the graph show results of measuring expression in single ears when the gene was introduced into elite LH 283 and LH287, supra. The unshaded bars shows expression levels when introduced into the high oil germplasm HOC, supra, which again provided higher expression levels.

Thus it can be seen the invention achieves at least all of its objectives.

What is claimed is:

1. A method of increasing expression of a heterologous protein in plant seed, comprising
   (a) introducing a recombinant nucleotide sequence encoding the protein operably linked to a promoter that is preferably expressed in plant seed tissue or expresses in seed as well as in other plant tissue into a maize plant, wherein the maize plant produces seed having an oil content greater than about 5.1 percent on a dry weight basis, such that the ratio of heterologous protein to total protein measured on a dry weight basis in seed of said maize plant increases compared to a maize plant producing seed not having an oil content greater than about 5.1 percent on a dry weight basis;
   (b) harvesting seed of said maize plant wherein said seed has an oil content greater than about 5.1 percent on a dry weight basis.

2. The method of claim 1 further comprising crossing the maize plant of step (a) with a second maize plant having increased seed oil content to produce progeny.

3. The method of claim 2 wherein the progeny are crossed with a third maize plant variety which has reduced levels of alcohol soluble proteins in the endosperm.

4. The method of claim 3 wherein the third plant has an endosperm that is opaque.

5. The method of claim 3, wherein the third plant is an opaque-2 plant.

6. A method of increasing expression and production of a heterologous protein expressed in plant seed tissue, comprising
   (a) introducing a recombinant nucleotide sequence encoding the heterologous protein operably linked to a promoter that is preferably expressed in plant seed tissue or expresses in seed as well as in other plant tissue into a plurality of maize plants, wherein the maize plant is produced from seed having an oil content greater than about 5.1 percent on a dry weight basis, such that the ratio of heterologous protein to total soluble protein measured on a dry weight basis in seed of the plant increases compared to a maize plant having seed not having an oil content greater than about 5.1 percent on a dry weight basis;
   (b) ascertaining the percent total soluble protein of the heterologous protein and;
   (c) separating the seed tissue of the plants from other plant tissue, or extracting the heterologous protein from the seed tissue.

* * * * *